United States Patent
Van Stee

(10) Patent No.: US 11,185,048 B2
(45) Date of Patent: Nov. 30, 2021

(54) HYBRID TOMATO VARIETY 'ESPARTANO'

(71) Applicant: Enza Zaden Beheer B.V., Enkhuizen (NL)

(72) Inventor: Martijn Petrus Van Stee, Lelystad (NL)

(73) Assignee: Enza Zaden Beheer B.V., Enkhuizen (NL)

( * ) Notice: Subject to any disclaimer, the term of this patent is extended or adjusted under 35 U.S.C. 154(b) by 0 days.

(21) Appl. No.: 16/917,082

(22) Filed: Jun. 30, 2020

(65) Prior Publication Data

US 2021/0000062 A1 Jan. 7, 2021

Related U.S. Application Data

(60) Provisional application No. 62/869,357, filed on Jul. 1, 2019.

(51) Int. Cl.
  *A01H 5/08* (2018.01)
  *A01H 1/00* (2006.01)
  *A01H 6/82* (2018.01)

(52) U.S. Cl.
  CPC .............. *A01H 6/825* (2018.05); *A01H 5/08* (2013.01)

(58) Field of Classification Search
  None
  See application file for complete search history.

(56) References Cited

U.S. PATENT DOCUMENTS

| | | | |
|---|---|---|---|
| 5,523,520 A | 6/1996 | Hunsperger | |
| 7,807,886 B2 | 10/2010 | Fowler | |
| 7,906,712 B2 | 3/2011 | Herlaar et al. | |
| 7,923,608 B2 | 4/2011 | Herlaar et al. | |
| 7,943,832 B2 | 5/2011 | Cook | |
| 8,097,789 B2 | 1/2012 | Heath | |
| 9,220,209 B2 | 12/2015 | Mooij | |
| 9,288,952 B2 | 3/2016 | Sisson | |
| 2007/0180572 A1 | 8/2007 | Fernandez | |
| 2009/0313715 A1 | 12/2009 | Herlaar et al. | |
| 2009/0313716 A1 | 12/2009 | Herlaar et al. | |
| 2010/0043085 A1 | 2/2010 | Herlaar | |
| 2010/0306870 A1 | 12/2010 | Herlaar | |
| 2014/0245470 A1 | 8/2014 | Kazokas | |
| 2014/0373189 A1 | 12/2014 | Mooij | |
| 2015/0074838 A1 | 3/2015 | Sisson | |
| 2018/0295802 A1* | 10/2018 | Petersen | C12N 15/8289 |
| 2019/0124879 A1 | 5/2019 | Van Stee | |

OTHER PUBLICATIONS

Enza Zaden USA, Inc. Jan. 2020. 'Espartano F1 '. Vegetable Seed Catalogue USA & Canada 2020, p. 66. Available online at <https://webkiosk.enzazaden.com/catalogue-USA-2020/62983894>. Obtained on 2 Jun. 5, 2020. 1 page.
Enza Zaden. "Tomato Rootstock Espartano F1". Products & Services. Available online at Khttps://www.enzazaden.com/US/products-and-services/our-products/Rootstock/Espartano%20F1>. Obtained on Jun. 25, 2020. 1 page.
Eshed, et al., (1996). "Less-than-additive epistatic interactions of quantitative trait loci in tomato," Genetics, 143:1807-1817.
Kraft, et al., (2000). "Linkage disequilibrium and fingerprinting in sugar beet," Theor. Appl. Genet., 101:323-326.

* cited by examiner

*Primary Examiner* — Phuong T Bui
(74) *Attorney, Agent, or Firm* — Morrison & Foerster LLP

(57) ABSTRACT

Hybrid tomato rootstock variety designated 'Espartano' is disclosed. The invention further relates to the seeds of hybrid tomato rootstock 'Espartano', to the plants of hybrid tomato rootstock 'Espartano', to methods for producing plants using the hybrid tomato rootstock 'Espartano', and to methods for producing other rootstock tomato lines, cultivars, or hybrids derived from the hybrid tomato rootstock 'Espartano'.

13 Claims, 20 Drawing Sheets
(20 of 20 Drawing Sheet(s) Filed in Color)

HYBRID TOMATO VARIETY 'ESPARTANO'

CROSS-REFERENCE TO RELATED APPLICATION

This application claims the benefit of U.S. Provisional Application No. 62/869,357, filed Jul. 1, 2019, which is hereby incorporated by reference in its entirety.

FIELD

The present disclosure relates to the field of plant breeding. In particular, the present disclosure relates to a new and distinctive tomato, *Solanum lycopersicum*, hybrid variety designated 'E15T41376', as well as a hybrid tomato (*Solanum lycopersicum* L. x *Solanum habrochaites* S. Knapp & D. M. Spooner) rootstock variety designated 'Espartano'.

BACKGROUND

Cultivated and commercial forms of tomato belong to the large and diverse genus *Solanum*, which also includes many other flowering plants such as nightshades, potato, and eggplant. It is believed that the tomato species, *Solanum lycopersicum*, originated in the Americas, being native to Ecuador, Peru and the Galapagos Islands, and was initially cultivated by Aztecs and Incas as early as 700 AD. Mexico appears to have been the site of domestication and the source of the earliest introduction. It is thought that the cherry tomato, *S. lycopersicum* var. *cerasiforme*, is the direct ancestor of modern cultivated forms.

As a crop, tomato is grown for its fruit, which is widely used as a fresh market or processed product. The size of tomato fruits may range from small to large, and there are cherry, plum, pear, standard, and beefsteak types. Tomato is grown commercially wherever environmental conditions permit the production of an economically viable yield. For example, in the United States, over 500,000 acres of tomatoes are grown annually, with approximately 40% of tomatoes being grown for fresh market consumption and the rest for processing. The largest market for processing tomatoes in the United States is in California, where processing tomatoes are harvested by machine. California is also the second largest fresh market for tomatoes, the majority of which are harvested by hand at vine ripe and mature green stages of ripeness. Fresh market tomatoes are available in the United States year round. Processing tomato season in California is from late June to September.

*S. lycopersicum* is a simple diploid species with twelve pairs of differentiated chromosomes. The cultivated tomato is self-fertile and almost exclusively self-pollinating. The tomato flowers are hermaphrodites. Commercial cultivars were initially open-pollinated, but most have now been replaced by better yielding hybrids. Due to its wide dissemination and high value, tomato has been intensively bred.

Tomatoes may be grouped by the amount of time it takes for the plants to mature fruit for harvest; in general the cultivars are classified as early, midseason or late-maturing. Tomatoes can also be grouped by the plant's growth habit, which can be determinate or indeterminate. Determinate plants tend to grow their foliage first, then set flowers that mature into fruit if pollination is successful. All of the fruit tend to ripen on a plant at about the same time. Indeterminate tomatoes start out by growing some foliage, then continue to produce foliage and flowers throughout the growing season. These plants tend to have tomato fruit in different stages of maturity at any given time. Recent developments in tomato breeding have led to a wider array of fruit color; in addition to the standard red ripe color, tomatoes can be creamy white, lime green, pink, yellow, golden, or orange.

Tomato grafting has been utilized in Asia and Europe for greenhouse and high tunnel production and is gaining popularity in the United States. One advantage of grafting is that it allows the use of rootstocks to provide or increase resistance against, for example, fungal and viral diseases. In addition to providing or increasing resistance against such diseases, the use of grafting may also increase tolerance against different abiotic stresses, such as drought tolerance, salinity tolerance, flooding tolerance, and heat and cold temperature tolerance. There are several methods for grafting tomatoes. The most common grafting methods include tongue approach/approach graft, hole insertion/terminal/top insertion graft, one cotyledon/slant/splice/tube graft, and cleft/side insertion graft.

Tomato is an important and valuable field crop. Thus, there is a continued need for new tomato varieties. In particular, there is a need for improved tomato varieties that are stable, high yielding, and agronomically sound.

BRIEF SUMMARY

In order to meet these needs, the present disclosure is directed to improved hybrid tomato varieties.

As used herein tomato variety 'E15T41376' is the same tomato variety as tomato variety 'E15T.41376' having NCIMB Accession Number X2 and disclosed in U.S. Provisional Application No. 62/869,357. While the name has changed, tomato variety 'E15T41376' has all the defining characteristics of tomato variety 'E15T.41376'.

In one embodiment, the present disclosure is directed to a hybrid tomato, *Solanum lycopersicum*, seed designated as 'E15T41376' having NCIMB Accession Number X2. In one embodiment, the present disclosure is directed to a *Solanum lycopersicum* tomato plant and parts isolated therefrom produced by growing 'E15T41376' tomato seed. In another embodiment, the present disclosure is directed to a *Solanum lycopersicum* plant and parts isolated therefrom having all the physiological and morphological characteristics of a *Solanum lycopersicum* plant produced by growing 'E15T41376' tomato seed having NCIMB Accession Number X2. In still another embodiment, the present disclosure is directed to an $F_1$ hybrid *Solanum lycopersicum* tomato seed, plants grown from the seed, and fruit isolated therefrom having 'E15T41376' as a parent, where 'E15T41376' is grown from 'E15T41376' tomato seed having NCIMB Accession Number X2.

Tomato plant parts include tomato leaves, ovules, pollen (pollen grains), seeds, tomato fruits, parts of tomato fruits, flowers, cells, and the like. In one embodiment, the present disclosure is directed to tomato leaves, ovules, pollen, seeds, tomato fruits, parts of tomato fruits, flowers and/or cells isolated from 'E15T41376' tomato plants. In certain embodiments, the present disclosure is further directed to pollen or ovules isolated from 'E15T41376' tomato plants. In another embodiment, the present disclosure is further directed to protoplasts produced from 'E15T41376' tomato plants. In another embodiment, the present disclosure is further directed to tissue culture of 'E15T41376' tomato plants, and to tomato plants regenerated from the tissue culture, where the plant has all of the morphological and physiological characteristics of 'E15T41376' tomato. In certain embodiments, tissue culture of 'E15T41376' tomato plants is produced from a plant part selected from leaf, anther, pistil, stem, petiole, root, root tip, fruit, seed, flower, cotyledon, hypocotyl, embryo and meristematic cell.

In another embodiment, the present disclosure is further directed to a method of selecting tomato plants, by a) growing 'E15T41376' tomato plants where the 'E15T41376' plants are grown from tomato seed having NCIMB Accession Number X2 and b) selecting a plant from step a). In another embodiment, the present disclosure is further directed to tomato plants, plant parts and seeds produced by the tomato plants where the tomato plants are isolated by the selection method described using 'E15T41376' tomato plants.

In another embodiment, the present disclosure is further directed to a method of making tomato seeds by crossing a tomato plant grown from 'E15T41376' tomato seed having NCIMB Accession Number X2 with another tomato plant, and harvesting seed therefrom. In still another embodiment, the present disclosure is further directed to tomato plants, tomato parts from the tomato plants, and seeds produced therefrom where the tomato plant is grown from seed produced by the method of making tomato seed described using 'E15T41376' tomato plants.

In another embodiment, the present disclosure is further directed to a method of making hybrid tomato 'E15T41376' by selecting seeds from the cross of one 'E15T41376' plant with another 'E15T41376' plant, a sample of 'E15T41376' tomato seed having been deposited under NCIMB Accession Number X2.

According to the present disclosure, there is provided a hybrid tomato plant designated as 'E15T41376'. This disclosure thus relates to the seeds of hybrid tomato 'E15T41376', to the plants of hybrid tomato 'E15T41376', as well as to methods for producing a tomato plant produced by crossing hybrid tomato 'E15T41376' with itself or another tomato plant. This disclosure also relates to methods for producing other tomato cultivars or hybrids derived from hybrid tomato 'E15T41376', and to the tomato cultivars and hybrids derived by the use of those methods. This disclosure further relates to tomato seeds and plants produced by crossing hybrid tomato 'E15T41376' with another tomato cultivar.

In another embodiment, the present disclosure is directed to single gene converted plants of hybrid tomato 'E15T41376'. The single transferred gene may preferably be a dominant or recessive allele. Preferably, the single transferred gene will confer such trait as sex determination, herbicide resistance, insect resistance, resistance for bacterial, fungal, or viral disease, improved harvest characteristics, enhanced nutritional quality, or improved agronomic quality.

In one embodiment, the present disclosure is directed to a hybrid tomato, *Solanum lycopersicum* L. x *Solanum habrochaites* S. Knapp & D. M. Spooner, seed designated as 'Espartano' having NCIMB Accession Number 43655. In one embodiment, the present disclosure is directed to a *Solanum lycopersicum* L. x *Solanum habrochaites* S. Knapp & D. M. Spooner tomato plant, and parts isolated therefrom produced by growing 'Espartano' tomato seed. In another embodiment, the present disclosure is directed to a *Solanum lycopersicum* L. x *Solanum habrochaites* S. Knapp & D. M. Spooner plant and parts isolated therefrom having all the physiological and morphological characteristics of a *Solanum lycopersicum* L. x *Solanum habrochaites* S. Knapp & D. M. Spooner plant produced by growing 'Espartano' tomato seed having NCIMB Accession Number 43655. In still another embodiment, the present disclosure is directed to an $F_1$ hybrid tomato seed, plants grown from the seed, and rootstocks isolated therefrom having 'Espartano' as a parent, where 'Espartano' is grown from 'Espartano' tomato seed having NCIMB Accession Number 43655.

Tomato plant parts include tomato rootstocks, leaves, ovules, pollen (pollen grains), seeds, tomato fruits, parts of tomato fruits, flowers, cells, and the like. In one embodiment, the present disclosure is directed to tomato rootstocks, leaves, ovules, pollen, seeds, tomato fruits, parts of tomato fruits, flowers and/or cells isolated from 'Espartano' tomato plants. In another embodiment, the present disclosure is directed to tomato rootstocks isolated from 'Espartano' tomato plants. In certain embodiments, the present disclosure is further directed to pollen or ovules isolated from 'Espartano' tomato plants. In another embodiment, the present disclosure is further directed to protoplasts produced from 'Espartano' tomato plants. In another embodiment, the present disclosure is further directed to tissue culture of 'Espartano' tomato plants, and to tomato plants regenerated from the tissue culture, where the plant has all of the morphological and physiological characteristics of 'Espartano' tomato. In certain embodiments, tissue culture of 'Espartano' tomato plants is produced from a plant part selected from leaf, anther, pistil, stem, petiole, root, root tip, fruit, seed, flower, cotyledon, hypocotyl, embryo and meristematic cell.

In another embodiment, the present disclosure is further directed to a method of selecting tomato plants, by a) growing 'Espartano' tomato plants where the 'Espartano' plants are grown from tomato seed having NCIMB Accession Number 43655 and b) selecting a plant from step a). In another embodiment, the present disclosure is further directed to tomato plants, plant parts and seeds produced by the tomato plants where the tomato plants are isolated by the selection method described using 'Espartano' tomato plants.

In another embodiment, the present disclosure is further directed to a method of making tomato seeds by crossing a tomato plant grown from 'Espartano' tomato seed having NCIMB Accession Number 43655 with another tomato plant, and harvesting seed therefrom. In still another embodiment, the present disclosure is further directed to tomato plants, tomato parts from the tomato plants, and seeds produced therefrom where the tomato plant is grown from seed produced by the method of making tomato seed described using 'Espartano' tomato plants.

In another embodiment, the present disclosure is further directed to a method of making hybrid tomato 'Espartano' by selecting seeds from the cross of one 'Espartano' plant with another 'Espartano' plant, a sample of 'Espartano' tomato seed having been deposited under NCIMB Accession Number 43655.

In another embodiment, the present disclosure is further directed to a tomato plant having a rootstock from 'Espartano' and a scion engrafted onto the rootstock, a sample of 'Espartano' tomato seed having been deposited under NCIMB Accession Number 43655.

According to the present disclosure, there is provided a hybrid tomato plant designated as 'Espartano'. This disclosure thus relates to the seeds of hybrid tomato 'Espartano', to the plants of hybrid tomato 'Espartano', to the rootstock of hybrid tomato 'Espartano', as well as to methods for producing a tomato plant produced by crossing hybrid tomato 'Espartano' with itself or another tomato plant. This disclosure also relates to methods for producing other tomato cultivars or hybrids derived from hybrid tomato 'Espartano', and to the tomato cultivars and hybrids derived by the use of those methods. This disclosure further relates to tomato seeds and plants produced by crossing hybrid tomato 'Espartano' with another tomato cultivar.

In another embodiment, the present disclosure is directed to single gene converted plants of hybrid tomato 'Espartano'. The single transferred gene may preferably be a dominant or recessive allele. Preferably, the single transferred gene will confer such trait as sex determination, herbicide resistance, insect resistance, resistance for bacterial, fungal, or viral disease, improved harvest characteristics, enhanced nutritional quality, or improved agronomic quality.

In another embodiment, the present disclosure is directed to methods for developing tomato plants in a tomato plant breeding program using plant breeding techniques including recurrent selection, backcrossing, pedigree breeding, restriction fragment length polymorphism enhanced selection, and genetic marker enhanced selection. Marker loci such as restriction fragment polymorphisms or random amplified DNA have been published for many years and may be used for selection (See, Pierce et al., HortScience (1990) 25:605-615; Wehner T., Cucurbit Genetics Cooperative Report, (1997) 20: 66-88; and Kennard et al., Theoretical Applied Genetics (1994) 89:217-224). Seeds, tomato plants, and parts thereof produced by such breeding methods are also part of the disclosure.

In addition to the exemplary aspects and embodiments described above, further aspects and embodiments will become apparent by study of the following descriptions.

BRIEF DESCRIPTION OF THE DRAWINGS

The patent or application file contains at least one drawing executed in color. Copies of this patent or patent application publication with color drawings will be provided by the office upon request and payment of the necessary fee.

FIG. 1A shows stems with fruits of hybrid tomato 'E15T41376'. FIG. 1B shows a cross-section of a fruit of hybrid tomato 'E15T41376'. FIG. 1C shows a longitudinal section of a fruit of hybrid tomato 'E15T41376'. FIG. 1D shows the top of a full ripe fruit of hybrid tomato 'E15T41376' (on left) and the top of a green fruit of hybrid tomato 'E15T41376' (on right). FIG. 1E shows the bottom of a full ripe fruit of hybrid tomato 'E15T41376' (on left) and the bottom of a green fruit of hybrid tomato 'E15T41376' (on right). FIG. 1F shows the lower side of a leaf of hybrid tomato 'E15T41376'. FIG. 1G shows the upper side of a leaf of hybrid tomato 'E15T41376'. FIG. 1H shows flowers of hybrid tomato 'E15T41376'. FIG. 1I shows flowers and plants of hybrid tomato 'E15T41376'. FIG. 1J shows plants and fruit of hybrid tomato 'E15T41376'.

FIG. 2A shows a cross-section of a fruit of tomato variety 'Campari'. FIG. 2B shows a longitudinal section of a fruit of tomato variety 'Campari'. FIG. 2C shows the top of a full ripe fruit of tomato variety 'Campari' (on left) and the top of a green fruit of tomato variety 'Campari' (on right). FIG. 2D shows the bottom of a full ripe fruit of tomato variety 'Campari' (on left) and the bottom of a green fruit of tomato variety 'Campari' (on right). FIG. 2E shows the lower side of a leaf of tomato variety 'Campari'. FIG. 2F shows the upper side of a leaf of tomato variety 'Campari'. FIG. 2G shows flowers of tomato variety 'Campari'. FIG. 2H shows flowers and plants of tomato variety 'Campari'. FIG. 2I shows plants and fruit of tomato variety 'Campari'.

FIG. 5A shows a comparison of fruit size produced by scion 'Toretto' when grafted onto tomato rootstock 'Fortamino', hybrid tomato rootstock 'Espartano', and tomato rootstock 'Empower'. Fruit size was divided into small (S), medium (M), large (L), extra large (XL), and jumbo (J) (colors for each category are provided in legend on right; and the numbers above the bars indicate the number of fruit in each category). FIG. 5B shows a comparison of yield in kg/plant and boxes/Ha of scion 'Toretto' when grafted onto tomato rootstock 'Fortamino', hybrid tomato rootstock 'Espartano', and tomato rootstock 'Empower'. The numbers above the bars are the yield in kg/plant, and the numbers inside the bars are the yield in boxes/Ha.

DETAILED DESCRIPTION

Figure 1A:
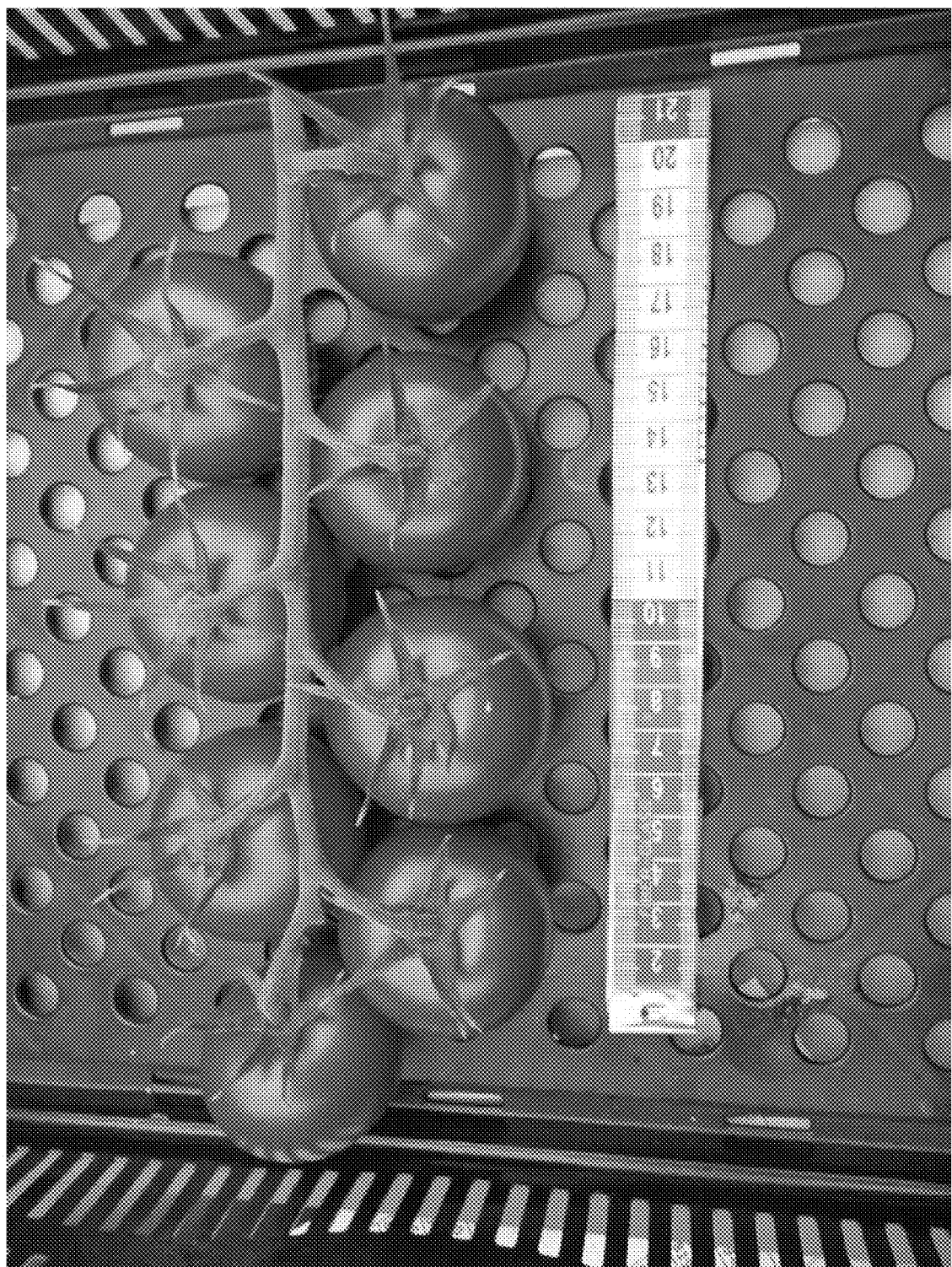
FIGS. 1A-1J show hybrid tomato 'E15T41376'.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The selected germplasm is crossed in order to recombine the desired traits and, through selection, varieties or parent lines are developed. The goal is to combine, in a single variety or hybrid, an improved combination of desirable traits from the parental germplasm. These important traits may include higher yield, field performance, fruit and agronomic quality such as firmness, color, content in soluble solids, acidity and viscosity, resistance to diseases and insects, and tolerance to drought and heat. As tomato fruits may be subject to mechanical harvesting for processing purposes, i.e., juice, paste, catsup, etc., uniformity of plant characteristics such as germination, growth rate, maturity and plant uniformity is also desirable.

Choice of breeding or selection methods can depend on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences the choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from pollinations, and the number of hybrid offspring from each successful cross.

Each breeding program may include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for at least three years. The best lines can then be candidates for new commercial cultivars. Those still deficient in a few traits may be used as parents to produce new populations for further selection. These processes, which lead to the final step of marketing and distribution, may take from eight to twelve years from the time the first cross or selection is made.

One goal of tomato breeding is to develop new, unique, and genetically superior tomato inbred lines and hybrids. A breeder can initially select and cross two or more parental lines, followed by repeated selfing and selection, producing many new genetic combinations. A plant breeder can then select which germplasms to advance to the next generation. These germplasms may then be grown under different geographical, climatic, and soil conditions, and further selections can be made during, and at the end of, the growing season. In the case of hybrid variety development, two parental lines may be crossed to produce $F_1$ progeny. A single-cross hybrid is produced when two inbred lines are crossed to produce an $F_1$ hybrid. Once the parental lines that give the best hybrid performance have been identified, the hybrid seed can be reproduced indefinitely as long as the homogeneity of the inbred parent is maintained. Alternatively, a hybrid tomato plant may also serve as a parent in the development of another hybrid tomato plant.

The development of commercial tomato varieties thus requires the development of tomato parental lines, the crossing of these lines, and the evaluation of the crosses. Various breeding methods may be used to develop tomato varieties from breeding populations and non-limiting examples of such methods are described herein. Breeding programs can be used to combine desirable traits from two or more varieties or various broad-based sources into breeding pools from which lines are developed by selfing and selection of desired phenotypes. The new lines are crossed with other lines and the hybrids from these crosses are evaluated to determine which have commercial potential.

Accordingly, the present disclosure is directed to new hybrid tomato 'E15T41376' and hybrid tomato rootstock 'Espartano'. Breeding methods involving 'E15T41376' and 'Espartano', as well as methods of producing and evaluating plants derived from 'E15T41376' and 'Espartano', are further described herein.

Definitions

In the description and tables that follow, a number of terms are used. In order to provide a clear and consistent understanding of the specification and claims, the following definitions are provided.

Allele: An allele is any of one or more alternative form of a gene, all of which relate to one trait or characteristic. In a diploid cell or organism, the two alleles of a given gene occupy corresponding loci on a pair of homologous chromosomes.

Attachment point: The point on the tomato fruit where the fruit is connected to the tomato plant.

Backcrossing: Backcrossing is a process in which a breeder repeatedly crosses hybrid progeny back to one of the parents, for example, a first generation hybrid $F_1$ with one of the parental genotype of the $F_1$ hybrid.

BRIX: Means a percentage by weight of the sugar in solution (e.g., from a fruit) measured using a refractometer, wherein the fruit is cut in half and the juice within the fruit is squeezed onto a lens. The juice on the lens is then measured by the refractometer.

Determinate tomato: A variety that comes to fruit all at once, then stops bearing. Determinate varieties are best suited for commercial growing since they can be harvested all at once.

Essentially all the physiological and morphological characteristics: A plant having essentially all the physiological and morphological characteristics of another plant means a plant having the physiological and morphological characteristics, except for the characteristics derived from the converted gene, of the other plant.

Flesh color: The color of the tomato flesh that can range from orange-red to dark red when at ripe stage (harvest maturity).

Fruit: A ripened ovary, together with any other structures that ripen with the ovary and form a unit.

Grafting: Grafting refers to attaching tissue from one plant to another plant so that the vascular tissues of the two tissues join together.

pH: The pH is a measure of acidity. A pH under 4.35 is desirable to prevent bacterial spoilage of finished products. pH rises as fruit matures.

Plant part: A plant part means any part of a plant including, for example, a cell, protoplast, embryo, pollen grain, ovule, flower, leaf, stem, cotyledon, hypocotyl, meristematic cell, rootstock, root, root tip, pistil, anther, shoot tip, shoot, fruit and petiole.

Predicted paste bostwick: The predicted paste bostwick is the flow distance of tomato paste diluted to 12 degrees brix and heated prior to evaluation. Dilution to 12 degrees brix for bostwick measurement is a standard method used by industry to evaluate product consistency. The lower the number, the thicker the product and therefore more desirable in consistency oriented products such as catsup. The following formula is usually used to evaluate the predicted paste bostwick: Predicted paste bostwick=−11.53+(1.64*juice brix)+(0.5*juice bostwick).

Regeneration: Regeneration refers to the development of a plant from tissue culture.

Relative maturity: Relative maturity is an indication of time until a tomato genotype is ready for harvest. A genotype is ready for harvest when 90% or more of the tomatoes are ripe.

Rootstock: A root and its associated growth buds, used as a stock in plant propagation. As disclosed herein, such roots may be selected from a plant, for example for the resistance of its roots to diseases or stress (e.g., heat, cold, salinity, etc.). The use of rootstocks may increase plant vigor (e.g., growth, productivity, etc.).

Scion: A part of a plant that is attached to a rootstock. A scion plant may be selected for its stems, leaves, flowers, or fruits. A selected scion may be used with the disclosed rootstock variety for greenhouse or open field, fresh market or processing tomatoes.

Semi-erect habit: A semi-erect plant has a combination of lateral and upright branching and has an intermediate-type habit between a prostate plant habit, having laterally growing branching with fruits most of the time on the ground, and an erect plant habit, having branching going straight up with fruit being off the ground.

Single gene converted: Single gene converted or conversion plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

Soluble Solids: Soluble solids refer to the percent of solid material found in the fruit tissue, the vast majority of which is sugars. Soluble solids are directly related to the finished processed product yield of pastes and sauces. Soluble solids are estimated with a refractometer, and measured as degrees brix.

Quantitative Trait Loci (QTL): Quantitative trait loci refer to genetic loci that control to some degree numerically representable traits that are usually continuously distributed.

Uniform ripening: Refers to a tomato that ripens uniformly, i.e., one that has no green discoloration on the shoulders. The uniform ripening is controlled by a single recessive gene.

Vegetative propagation: Refers to taking part of a plant and allowing that plant part to form roots where plant part is defined as leaf, pollen, embryo, cotyledon, hypocotyl, meristematic cell, root, root tip, pistil, anther, flower, shoot tip, shoot, stem, fruit and petiole.

Viscosity: The viscosity or consistency of tomato products is affected by the degree of concentration of the tomato, the amount and extent of degradation of pectin, the size, shape and quality of the pulp, and probably to a lesser extent, by the proteins, sugars and other soluble constituents. The viscosity is measured in Bostwick centimeters by using instruments such as a Bostwick Consistometer.

Overview of Hybrid Tomato 'E15T41376'

Figure 1B:
Figure 1C:
Figure 1D:
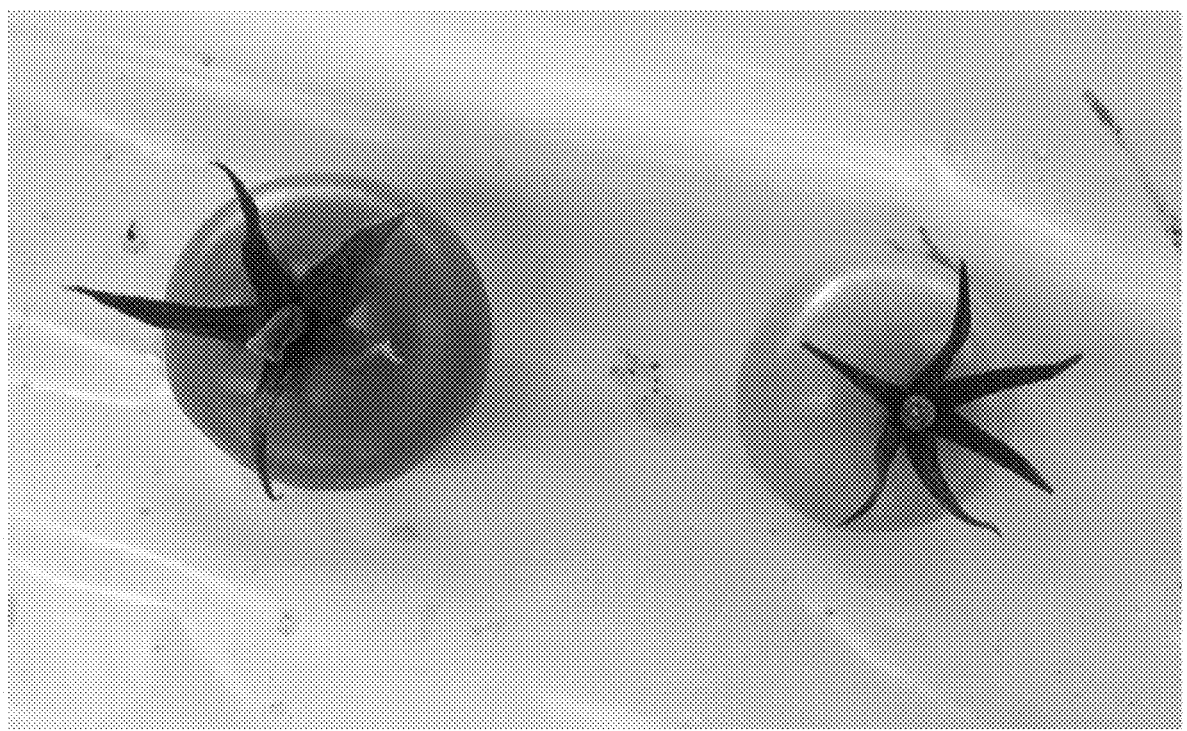
Figure 1E:
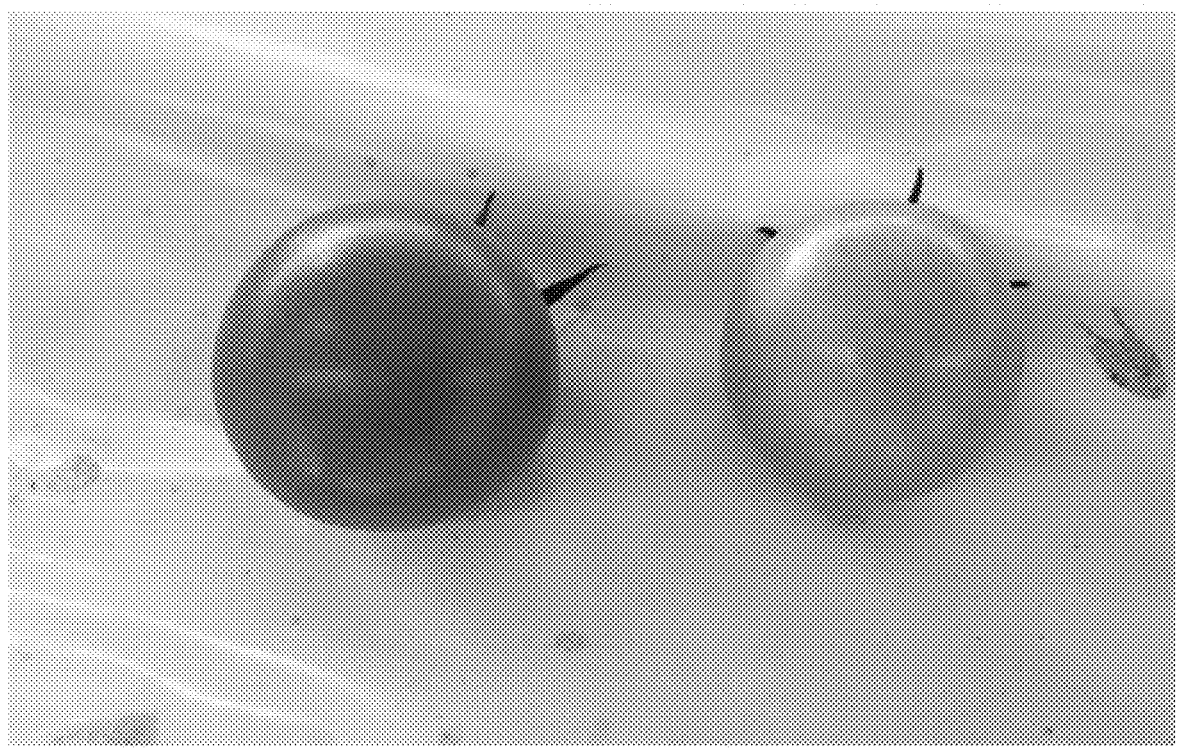
Figure 1F:
Figure 1G:
Figure 1H:
Figure 1I:
Figure 1J:
Figure 2A:
FIGS. 2A-2I show commercial tomato variety 'Campari' (unpatented).
Figure 2B:
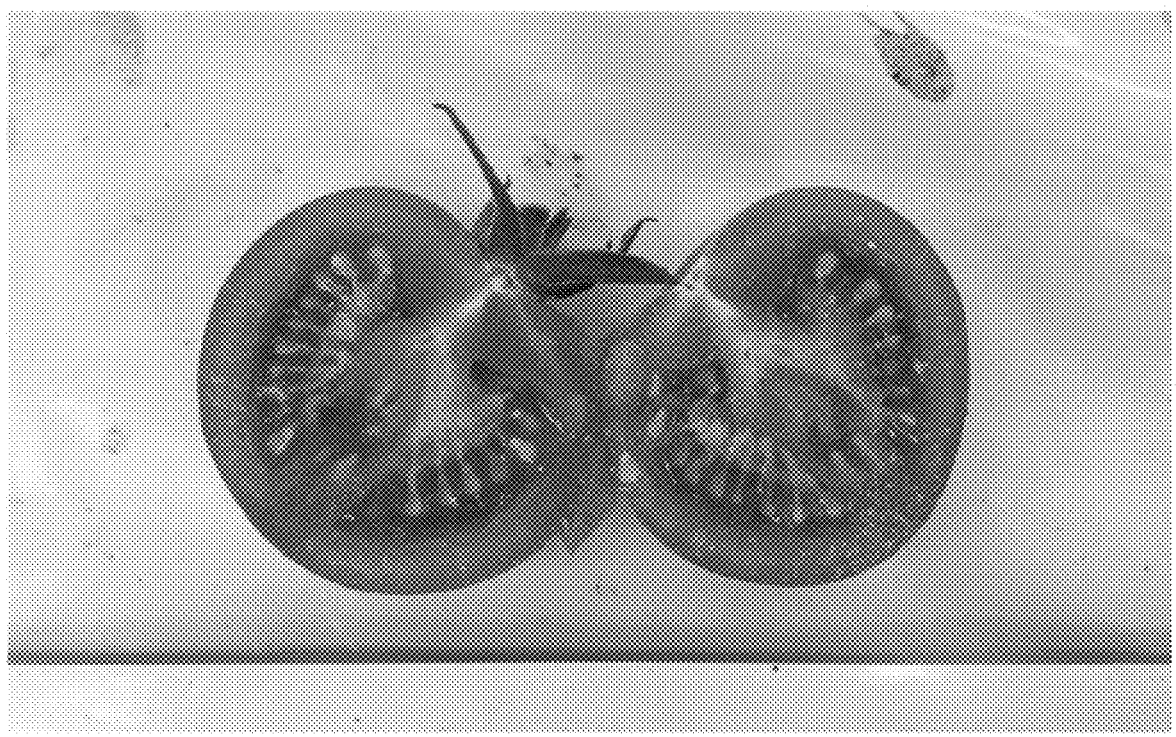
Figure 2C:
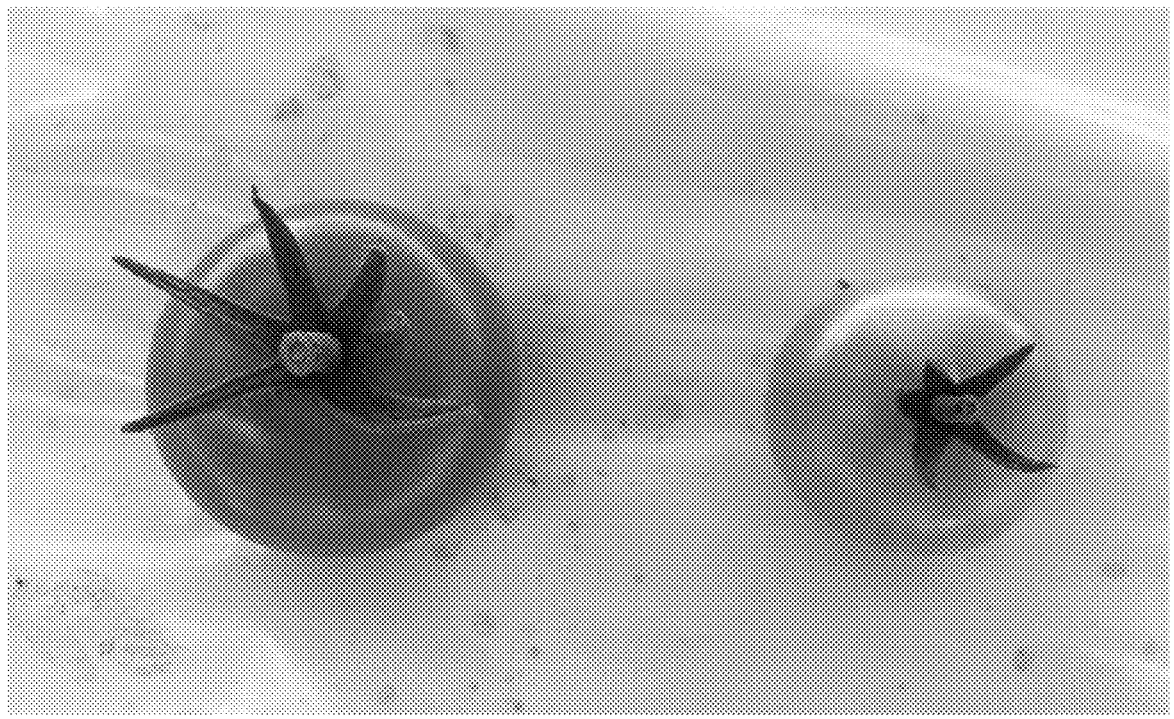
Figure 2D:
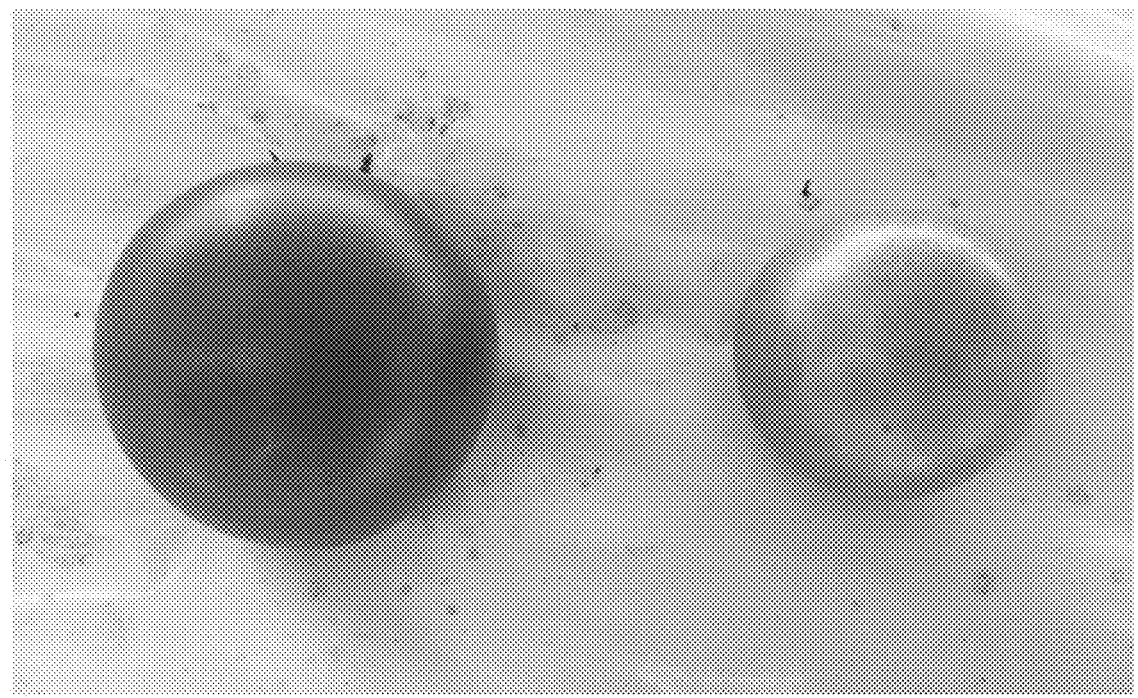
Figure 2E:
Figure 2F:
Figure 2G:
Figure 2H:
Figure 2I:

Hybrid tomato 'E15T41376' is seed propagated, has indeterminate growth, exhibits a medium early relative maturity when grown in a greenhouse, and produces mature fruits with a weight of 40 g to 45 g. 'E15T41376' is suitable for fresh market or garden use. In addition, hybrid tomato 'E15T41376' is highly resistant to Tobacco Mosaic Virus (TMV), Tomato Apex Necrosis Virus (ToANV), and *Oidium neolycopersici* (On) (ex *Oidium lycopersicum* (Ol)); resistant to *Verticillium* sp. (Va and Vd) race 0, *Fusarium oxysporum* f. sp. *lycopersici* (Fol) race 0 (ex1) and race 1 (ex2), *Fulvia fulva* (Ff) (ex *Cladosporium fulvum*) groups A, B, C, D, and E, Tomato Mosaic Virus (TMV) strains 0, 1, and 2, and Tomato Torrado Virus (ToTV); moderately resistant to root-knot nematodes *Meloidogyne incognita* (Mi), *Meloidogyne arenaria* (Ma), and *Meloidogyne javanica* (Mj); and susceptible to *Fusarium oxysporum* f sp. *radicis lycopersici* (For), Tomato Spotted Wilt Virus (TSWV), and *Pyrenochaeta lycopersici* (Pl). FIG. 1A depicts the stems and fruit of hybrid tomato 'E15T41376', FIGS. 1B-1C depict a cross-section and a longitudinal section of a fruit of hybrid tomato 'E15T41376', FIGS. 1D-1E depict the tops and bottoms of full ripe fruit and green fruit of hybrid tomato 'E15T41376', FIGS. 1F-1G depict the lower side and the upper side of leaves of hybrid tomato 'E15T41376', FIGS. 1H-1I depict flowers and plants of hybrid tomato 'E15T41376', and FIG. 1J depicts plants and fruits of hybrid tomato 'E15T41376'. Hybrid tomato 'E15T41376' is the result of numerous generations of plant selections from its parent lines, and was chosen for its fruit taste, truss performance, and yield potential.

Hybrid tomato 'E15T41376' has shown uniformity and stability for the traits, within the limits of environmental influence for the traits. The hybrid has been increased with continued observation for uniformity. No variant traits have been observed or are expected in hybrid tomato 'E15T41376'.

Objective Description of the Hybrid Tomato 'E15T41376'

'E15T41376' has the following morphologic and other characteristics as outlined in Table 1.

TABLE 1

Morphologic and other characteristics of 'E15T41376'.
Variety Description Information For 'E15T41376'

| SEEDLING: | |
|---|---|
| Anthocyanin in hypocotyl of 2-15 cm seedling: | Absent |
| Habit of 3-4 week old seedling: | Normal |
| MATURE PLANT: | |
| Growth type: | Indeterminate |
| Form: | Normal |
| Plant height: | Medium |
| Size of canopy: | Medium |
| Habit: | Sprawling (decumbent) |
| LSL gene(s): | Absent |
| Sensitivity to silvering: | Insensitive (tolerant to silvering) |

TABLE 1-continued

Morphologic and other characteristics of 'E15T41376'.
Variety Description Information For 'E15T41376'

GROWTH CONDITION:

| | |
|---|---|
| Type of culture: | Greenhouse; staked |
| Main use: | Fresh market or garden; truss |
| Machine harvest: | Not adapted |

STEM:

| | |
|---|---|
| Branching: | Sparse |
| Branching at cotyledonary or first node: | Present |
| Number of nodes between first inflorescence: | 7 to 10 |
| Number of nodes between early (first to second, second to third) inflorescences: | 3 to 4 |
| Number of nodes between later developing inflorescences: | 3 |
| Pubescence on younger stems: | Smooth (no long hairs) |

LEAF:

| | |
|---|---|
| Type of blade: | Tomato |
| Morphology: | Type 2 (bipinnate) |
| Intensity of green color: | Medium |
| Length: | Medium |
| Margin of major leaflets: | Shallowly toothed or scalloped |
| Margin rolling or wiltiness: | Absent |
| Onset of leaf rolling: | Mid season |
| Surface of major leaflets: | Smooth |
| Pubescence: | Smooth (no long hairs) |

INFLORESCENCE:

| | |
|---|---|
| Type: | Simple |
| Average number of flowers in inflorescence: | 9 to 11 |
| Leafy or "running" inflorescences: | Absent |

FLOWER:

| | |
|---|---|
| Calyx shape: | Normal, lobes awl-shaped |
| Calyx lobe length: | Shorter than corolla |
| Corolla color: | Yellow |
| Style pubescence: | Absent |
| Anthers: | All fused into tube |
| Fasciation (first flower of third inflorescence): | Absent |

PEDUNCLE:

| | |
|---|---|
| Abscission layer: | Present |

FRUIT:

| | |
|---|---|
| Typical fruit shape: | Oblate to circular |
| Shape in longitudinal section: | Oblate |
| Shape of transverse section: | Round |
| Shape of stem end: | Flat |
| Shape of blossom end: | Flat |
| Shape of pistil scar: | Dot |
| Ribbing at peduncle end: | Absent or very weak |
| Abscission layer: | Present (pedicellate) |
| Point of detachment of fruit at harvest: | At pedicel joint |
| Pedicel length (from joint to calyx attachment): | 3 mm |
| Length of mature fruit (stem axis): | 50 mm |
| Diameter of fruit at widest point: | 45 mm |
| Average weight of mature fruit: | 40 g to 45 g |
| Number of locules: | Only two |
| Fruit surface: | Smooth |
| Green shoulder (before maturity): | Absent |
| Green stripes (before maturity): | Absent |
| Full ripe fruit color: | Red |
| Full ripe fruit flesh color: | Red/Crimson |
| Uniformity of flesh color: | Uniform |
| Stem scar size: | Small |
| Core: | Present |
| Thickness of pericarp: | 5 mm |
| Firmness: | Firm |
| Soluble solids as °Brix: | 6.3 to 6.6 (differs with growing locations and seasons) |
| Fruit shelf-life: | Medium |

TABLE 1-continued

Morphologic and other characteristics of 'E15T41376'.
Variety Description Information For 'E15T41376'

PHENOLOGY:

| | |
|---|---|
| Number of days from seeding to 50% flowering: | 60 |
| Number of days from seeding to once over harvest: | 40 |
| Fruiting season length: | Long |
| Relative maturity when grown in greenhouse: | Medium early |

FRUIT DISORDER RESISTANCE:

| | |
|---|---|
| Blotchy ripening: | Highly resistant |
| Catface: | Highly resistant |
| Cracking, concentric: | Resistant, few symptoms in number and size |
| Cracking, radial: | Resistant, few symptoms |
| Bursting: | Highly resistant |
| Blossom end rot: | Highly resistant |
| Gold fleck: | Resistant, few symptoms |

DISEASE AND PEST RESISTANCE:

| | |
|---|---|
| *Meloidogyne incognita* (Mi) (root-knot nematode): | Moderately resistant |
| *Meloidogyne arenaria* (Ma) (root-knot nematode): | Moderately resistant |
| *Meloidogyne javanica* (Mj) (root-knot nematode): | Moderately resistant |
| *Verticillium* sp. (Va and Vd) race 0: | Resistant |
| *Fusarium oxysporum* f. sp. *lycopersici* race 0 (ex1) (Fol): | Resistant |
| *Fusarium oxysporum* f. sp. *lycopersici* race 1 (ex2): | Resistant |
| *Fusarium oxysporum* f. sp. *radicis lycopersici* (For): | Susceptible |
| *Fulvia fulva* (Ff) (ex *Cladosporium fulvum*) group A: | Resistant |
| *Fulvia fulva* (Ff) (ex *Cladosporium fulvum*) group B: | Resistant |
| *Fulvia fulva* (Ff) (ex *Cladosporium fulvum*) group C: | Resistant |
| *Fulvia fulva* (Ff) (ex *Cladosporium fulvum*) group D: | Resistant |
| *Fulvia fulva* (Ff) (ex *Cladosporium fulvum*) group E: | Resistant |
| Tomato Mosaic Virus (ToMV) strain 0: | Resistant |
| Tomato Mosaic Virus (ToMV) strain 1: | Resistant |
| Tomato Mosaic Virus (ToMV) strain 2: | Resistant |
| Tomato Spotted Wilt Virus (TSWV): | Susceptible |
| Tobacco Mosaic Virus (TMV): | Highly resistant |
| Tomato Torrado Virus (ToTV): | Resistant |
| Tomato Apex Necrosis Virus (ToANV): | Highly resistant |
| *Oidium neolycopersici* (On) (ex *Oidium lycopersicum* (Ol)): | Highly resistant |
| *Pyrenochaeta lycopersici* (Pl) (brown root rotor corky root): | Susceptible |

Comparison of Hybrid Tomato 'E15T41376' to Other Tomato Varieties

Hybrid tomato 'E15T41376' is similar to commercial tomato variety 'Campari' (unpatented). Column 1 of Table 2 shows the plant characteristics being compared, column 2 shows the characteristics of hybrid tomato 'E15T41376', and column 3 shows the characteristics of tomato 'Campari'. Further distinguishing features are apparent from the comparison of hybrid tomato 'E15T41376' depicted in FIGS. 1A-1J and commercial tomato variety 'Campari' depicted in FIGS. 2A-2I.

TABLE 2

Comparison of hybrid tomato 'E15T41376' to 'Campari'.

| Characteristic | 'E15T41376' | 'Campari' |
|---|---|---|
| Plant height | Medium | Short to medium |
| Leaf length | Medium | Small to medium |
| Intensity of the green color of the leaf | Medium | Light |
| Fruit size | Small | Medium |

Hybrid tomato 'E15T41376' is similar to commercial tomato variety 'Brioso' (unpatented). Column 1 of Table 3 shows the plant characteristics being compared, column 2 shows the characteristics of hybrid tomato 'E15T41376', and column 3 shows the characteristics of tomato 'Brioso'.

TABLE 3

Comparison of hybrid tomato 'E15T41376' to 'Brioso'.

| Characteristic | 'E15T41376' | 'Brioso' |
|---|---|---|
| Plant vigor | Weak | Strong |
| Fruit weight | 40 g-45 g | 38 g |
| °Brix | 6.6 | 6.3 |
| Fruit taste | More likeable (see Table 7) | Less likeable (see Table 7) |

Hybrid tomato 'E15T41376' is similar to commercial tomato variety 'Annaisa' (unpatented). Column 1 of Table 4 shows the plant characteristics being compared, column 2 shows the characteristics of hybrid tomato 'E15T41376', and column 3 shows the characteristics of tomato 'Annaisa'.

TABLE 4

Comparison of hybrid tomato 'E15T41376' to 'Annaisa'.

| Characteristic | 'E15T41376' | 'Annaisa' |
|---|---|---|
| Resistance to Tomato Apex Necrosis Virus (ToANV) | Highly resistant | Susceptible |
| Resistance to Fusarium oxysporum f. sp. radicis lycopersici (For) | Susceptible | Highly resistant |

Two trials were conducted in which the fruit taste profile, average fruit weight, and yield of tomato variety 'E15T41376' were compared with those of other varieties. In both trials, the fruit taste profile was assessed by Flavour Research Fruits & Vegetables, an independent research institute that is part of the Greenhouse Horticulture business unit of Wageningen University located in Bleiswijk, Netherlands (wur.nl/en/Research-Results/Research-Institutes/plant-research/greenhouse-horticulture/Research-themes/quality-production/flavour-research-fruit-vegetables/Flavour-research.htm). The overall "taste number" was obtained by combining several assessments, including the °brix, acids, % juice, and bite assessments, using proprietary methods.

Table 5 shows results of the first trial comparing the fruit taste profile of tomato varieties 'E15T41376', 'Timeax' (unpatented), and 'Annaisa' (unpatented). The fruit taste of 'E15T41476' was better than the fruit taste of 'Timeax' and 'Annaisa' due to the higher ° Brix.

TABLE 5

Comparison of the fruit taste profile of 'E15T41376', 'Timeax', and 'Annaisa' (first trial).

| Variety | Taste Number | °Brix | Acids | % Juice | Bite |
|---|---|---|---|---|---|
| 'E15T41376' | 62 | 6.3 | 7.1 | 44 | 86 |
| 'Timeax' | 58 | 5.6 | 7.1 | 53 | 119 |
| 'Annaisa' | 64 | 5.7 | 7.5 | 59 | 87 |

Figure 3:
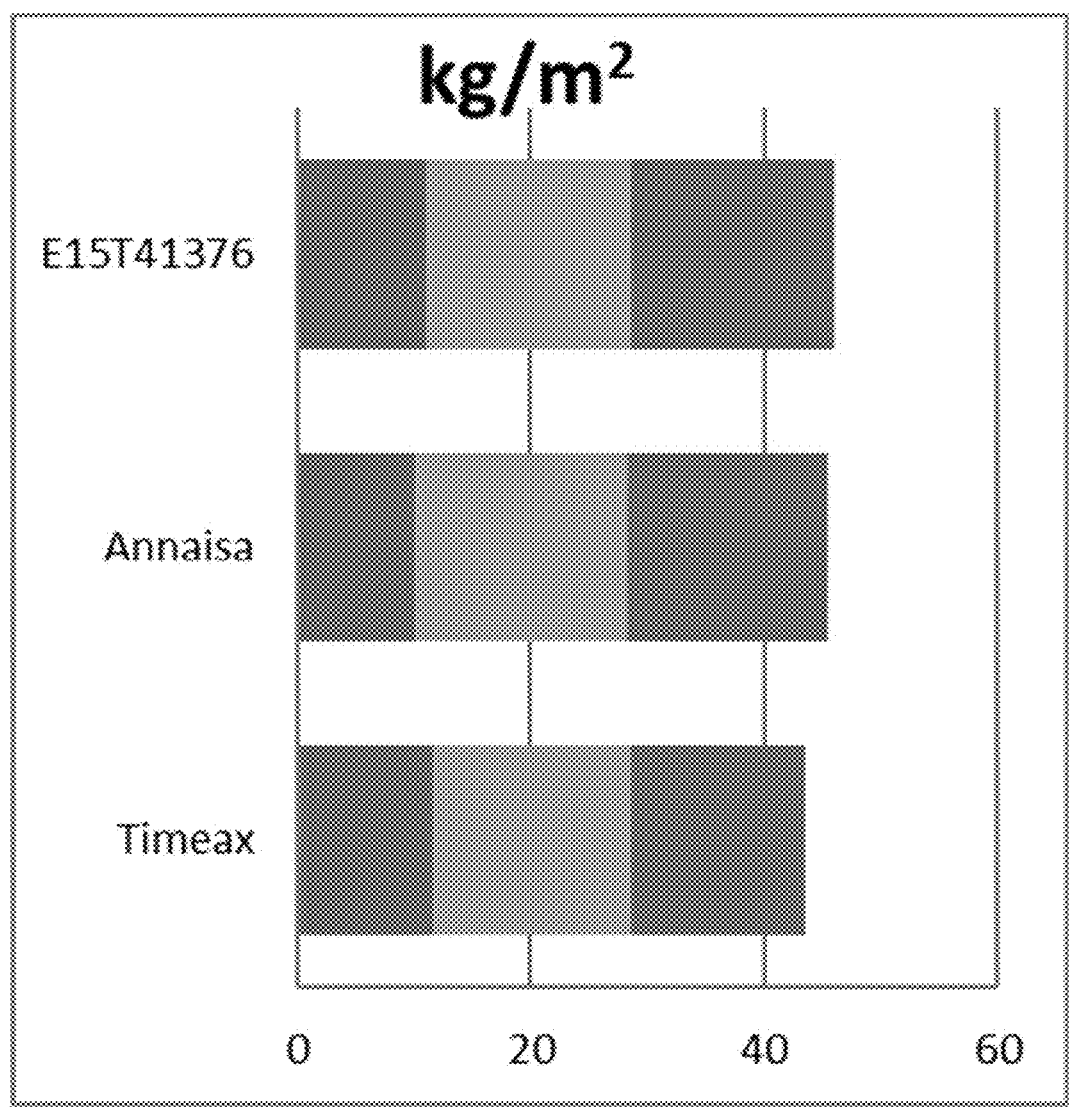
FIG. 3 shows results of a trial comparing the cumulative yield in kg/m$^2$ of hybrid tomato 'E15T41376', commercial tomato variety 'Annaisa' (unpatented), and commercial tomato variety 'Timeax' (unpatented) evaluated at different times over the Dutch growing season (artificial light season). Blue=sum of kg/m$^2$ from the first harvest (before October 16); red=sum of kg/m$^2$ from October 16 until December 27; green=sum of kg/m$^2$ from December 27 until April 30; and purple=sum of kg/m$^2$ from April 30 until end of season.

Table 6 shows results of the first trial comparing the average fruit weight and the cumulative yield of tomato varieties 'E15T41376', 'Timeax' (unpatented), and 'Annaisa' (unpatented) evaluated at different times over the Dutch growing season (artificial light season). FIG. 3 provides a graph of the cumulative yield of tomato varieties 'E15T41376', 'Timeax', and 'Annaisa' evaluated at different times over the Dutch growing season (artificial light season).

TABLE 6

Comparison of the average fruit weight and the yield of 'E15T41376', 'Timeax', and 'Annaisa' (first trial).

| | Average Fruit Weight (g) | | | Cumulative Yield (kg/m$^2$) | | | |
|---|---|---|---|---|---|---|---|
| Variety | Oct. 9 | Jan. 2 | Total | Oct. 16 | Dec. 27 | Apr. 30 | End |
| 'E15T41376' | 65 | 42 | 44 | 5.74 | 16.70 | 34.48 | 51.89 |
| 'Timeax' | 53 | 31 | 37 | 6.46 | 17.11 | 34.21 | 49.04 |
| 'Annaisa' | 51 | 34 | 38 | 5.00 | 14.99 | 33.28 | 50.42 |

Table 7 shows results of a second trial comparing the fruit taste profile of tomato varieties 'E15T41376', 'Campari' (unpatented), and 'Brioso' (unpatented). The fruit taste of 'E15T41476' was better than the fruit taste of 'Campari' and 'Brioso' due to the higher ° Brix.

TABLE 7

Comparison of the fruit taste profile of 'E15T41376', 'Campari', and 'Brioso' (second trial).

| Variety | Taste Number | °Brix | Acids | % Juice | Bite |
|---|---|---|---|---|---|
| 'E15T41376' | 61 | 6.6 | 7.2 | 33 | 74 |
| 'Campari' | 61 | 6.1 | 6.6 | 49 | 68 |
| 'Brioso' | 58 | 6.3 | 6.7 | 38 | 95 |

Table 8 shows results of a second trial comparing the average fruit weight and the yield of tomato varieties 'E15T41376', 'Campari', and 'Brioso'.

TABLE 8

Comparison of the average fruit weight and the yield of 'E15T41376', 'Campari', and 'Brioso' (second trial).

| Variety | Average Fruit Weight (g) | Yield (kg/m$^2$) |
|---|---|---|
| 'E15T41376' | 40-45 | 42.38 |
| 'Campari' | 43 | 44.98 |
| 'Brioso' | 38 | 39.57 |

Overview of Hybrid Tomato Rootstock 'Espartano'

Figure 4:
FIG. 4 shows a plant of hybrid tomato rootstock 'Espartano'.

Hybrid tomato rootstock 'Espartano' is seed propagated, exhibits tall plants, and produces very small fruit. In addition, hybrid tomato rootstock 'Espartano' is highly resistant to root-knot nematodes *Meloidogyne arenaria* (Ma), *Meloidogyne incognita* (Mi), and *Meloidogyne javanica* (Mj) and Tobacco Mosaic Virus (TMV) races 0, 1, and 2; resistant to *Verticillium* sp. (Va and Vd) race 0, *Fusarium oxysporum* f. sp. *lycopersici* (Fol) race 0 (ex1), race 1 (ex2), and race 2 (ex3), *Fusarium oxysporum* f sp. *radicis lycopersici* (For), *Fulvia fulva* (Ff) (ex *Cladosporium fulvum*) race 0 and groups A, B, C, D, and E, Tomato Mosaic Virus (TMV) strains 0, 1, and 2, Tomato Spotted Wilt Virus (TSWV), and *Pyrenochaeta lycopersici* (Pl); and susceptible to tomato yellows. Further, autonecrosis is absent in hybrid tomato rootstock 'Espartano'. A representative photograph of a plant of hybrid tomato rootstock 'Espartano' is shown in FIG. 4. Hybrid tomato rootstock 'Espartano' is the result of numerous generations of plant selections from its parent lines, and was chosen for its extreme plant vigor that lasts until the end of the season, and its resistance to soil-born pathogens.

Hybrid tomato rootstock 'Espartano' has shown uniformity and stability for the traits, within the limits of environmental influence for the traits. The hybrid has been increased with continued observation for uniformity. No variant traits have been observed or are expected in hybrid tomato rootstock 'Espartano'.

Hybrid tomato rootstock 'Espartano' is graft compatible with all tomato scion cultivars, and confers the resistances listed in Table 9 and strong plant vigor on grafted plants. The rootstock variety disclosed herein is unique in that it is useful for grafting all types of tomato. In addition, hybrid tomato rootstock 'Espartano' is particularly distinguished from other rootstock varieties by its resistance to *Fusarium oxysporum* f sp. *lycopersici* (Fol) race 0 (ex1), race 1 (ex2), and race 2 (ex3).

Objective Description of the Hybrid Tomato Rootstock 'Espartano'

Hybrid tomato rootstock 'Espartano' has the following morphologic and other characteristics as outlined in Table 9.

TABLE 9

Morphologic and other characteristics of hybrid tomato rootstock 'Espartano'.
Variety Description Information For 'Espartano'

| | |
|---|---|
| SEEDLING: | |
| Anthocyanin in hypocotyl of 2-15 cm seedling: | Present |
| Habit of 3-4 week old seedling: | Normal |
| MATURE PLANT: | |
| Plant height: | Tall; 1400 cm |
| Growth: | Indeterminate |
| Form: | Normal |
| Size of canopy: | Large |
| Habit: | Sprawling (decumbent) |
| Autonecrosis: | Absent |
| GROWTH CONDITION: | |
| Type of culture: | Both field and greenhouse |
| Main use: | Rootstock; fresh market or garden |
| Machine harvest: | Not adapted |
| STEM: | |
| Branching: | Sparse |
| Branching at cotyledonary or first node: | Present |
| Number of nodes between first inflorescence: | 7 to 10 |
| Number of nodes between early (first to second, second to third) inflorescences: | 3 to 4 |
| Number of nodes between later developing inflorescences: | 3 |
| Pubescence on younger stems: | Moderately hairy |
| LEAF: | |
| Type: | Tomato |
| Morphology: | Type 2 (bipinnate) |
| Intensity of green color: | Dark |
| Margin of major leaflets: | Shallowly toothed or scalloped |
| Margin rolling or wiltiness: | Slight |
| Onset of leaf rolling: | Mid season |
| Surface of major leaflets: | Rugose (bumpy or veiny) |
| Pubescence: | Hirsute |
| INFLORESCENCE: | |
| Type: | Simple |
| Average number of flowers in inflorescence: | 8 to 10 |
| Leafy or 'running' inflorescences: | Occasional |
| FLOWER: | |
| Calyx shape: | Normal, lobes awl-shaped |
| Calyx lobe length: | Approximately equaling corolla |
| Corolla color: | Yellow |
| Style pubescence: | Dense |

TABLE 9-continued

Morphologic and other characteristics of hybrid tomato rootstock 'Espartano'.
Variety Description Information For 'Espartano'

| | |
|---|---|
| Anthers: | Separating into two or more groups at anthesis |
| Fasciation (first flower of third inflorescence): | Occasionally present |
| FRUIT: | |
| Typical fruit shape: | Circular |
| Shape in longitudinal section: | Circular |
| Shape of transverse section: | Round |
| Shape of stem end: | Flat |
| Shape of blossom end: | Flat |
| Shape of pistil scar: | Dot |
| Ribbing at peduncle end: | Absent or very weak |
| Abscission layer: | Present (pedicellate) |
| Point of detachment of fruit at harvest: | At calyx attachment |
| Pedicel length (from joint to calyx attachment): | 2 mm |
| Length of mature fruit (stem axis): | 3 mm |
| Diameter of fruit at widest point: | 12 mm |
| Average weight of mature fruit: | 10 g |
| Number of locules: | Only two |
| Fruit surface: | Smooth |
| Green shoulder (before maturity): | Present |
| Green shoulder color: | Yellow green |
| Full ripe fruit color: | Yellow |
| Full ripe fruit flesh color: | Yellow |
| Uniformity of flesh color: | Uniform |
| Stem scar size: | Small |
| Core: | Coreless (absent or smaller than 6 × 6 mm) |
| Thickness of pericarp: | 1 mm |
| Firmness: | Medium |
| Fruit shelf-life: | Medium |
| PHENOLOGY: | |
| Number of days from seeding to 50% flowering: | 62 |
| Number of days from seeding to once over harvest: | 40 |
| Fruiting season length: | Long |
| Relative maturity when grown in greenhouse: | Medium early |
| FRUIT DISORDER RESISTANCE: | |
| Catface: | Highly resistant |
| Cracking, concentric: | Resistant, few symptoms in number and size |
| Cracking, radial: | Resistant, few symptoms in number and size |
| Bursting: | Resistant, few symptoms |
| Blossom end rot: | Highly resistant |
| Graywall: | Highly resistant |
| Zippering: | Highly resistant |
| Gold fleck: | Intermediate susceptible |
| DISEASE AND PEST RESISTANCE: | |
| *Meloidogyne incognita* (Mi) (root-knot nematode): | Highly resistant |
| *Meloidogyne arenaria* (Ma) (root-knot nematode): | Highly resistant |
| *Meloidogyne javanica* (Mj) (root-knot nematode): | Highly resistant |
| *Verticillium* sp. (Va and Vd) race 0: | Resistant |
| *Fusarium oxysporum* f. sp. *lycopersici* race 0 (ex1) (Fol): | Resistant |
| *Fusarium oxysporum* f. sp. *lycopersici* race 1 (ex2) (Fol): | Resistant |
| *Fusarium oxysporum* f. sp. *lycopersici* race 2 (ex3) (Fol): | Resistant |
| *Fusarium oxysporum* f. sp. radicis *lycopersici* (For): | Resistant |
| *Fulvia fulva* (Ff) (ex *Cladosporium fulvum*) race 0: | Resistant |
| *Fulvia fulva* (Ff) (ex *Cladosporium fulvum*) group A: | Resistant |
| *Fulvia fulva* (Ff) (ex *Cladosporium fulvum*) group B: | Resistant |
| *Fulvia fulva* (Ff) (ex *Cladosporium fulvum*) group C: | Resistant |

TABLE 9-continued

Morphologic and other characteristics of hybrid tomato rootstock 'Espartano'.
Variety Description Information For 'Espartano'

| | |
|---|---|
| *Fulvia fulva* (Ff) (ex *Cladosporium fulvum*) group D: | Resistant |
| *Fulvia fulva* (Ff) (ex *Cladosporium fulvum*) group E: | Resistant |
| Tomato Mosaic Virus (ToMV) strain 0: | Resistant |
| Tomato Mosaic Virus (ToMV) strain 1: | Resistant |
| Tomato Mosaic Virus (ToMV) strain 2: | Resistant |
| Tomato Spotted Wilt Virus (TSWV): | Resistant |
| Tobacco Mosaic Virus (TMV) race 0: | Highly resistant |
| Tobacco Mosaic Virus (TMV) race 1: | Highly resistant |
| Tobacco Mosaic Virus (TMV) race 2: | Highly resistant |
| Tomato Yellows (tomato yellow leaf curl disease, TYLCD): | Susceptible |
| *Pyrenochaeta lycopersici* (Pl) (brown root rotor corky root): | Resistant, few symptoms in number and size |

Comparison of Hybrid Tomato Rootstock 'Espartano' to Other Tomato Rootstock Varieties Hybrid tomato rootstock 'Espartano' is similar to tomato rootstocks 'Maxifort' (unpatented) and 'DROI141' (unpatented). Column 1 of Table 10 shows the plant characteristic being compared, column 2 shows the characteristics of hybrid tomato rootstock 'Espartano', column 3 shows the characteristics of tomato rootstock 'Maxifort', and column 4 shows the characteristics of tomato rootstock 'DROI141'.

TABLE 10

Comparison of hybrid tomato rootstock 'Espartano' to tomato rootstocks 'Maxifort' and 'DROI141'.

| Characteristic | 'Espartano' | 'Maxifort' | 'DROI141' |
|---|---|---|---|
| Resistance to *Fusarium oxysporum* f. sp. *lycopersici* (Fol) races 0-2 | Resistant | Susceptible | Susceptible |

Figure 5A:
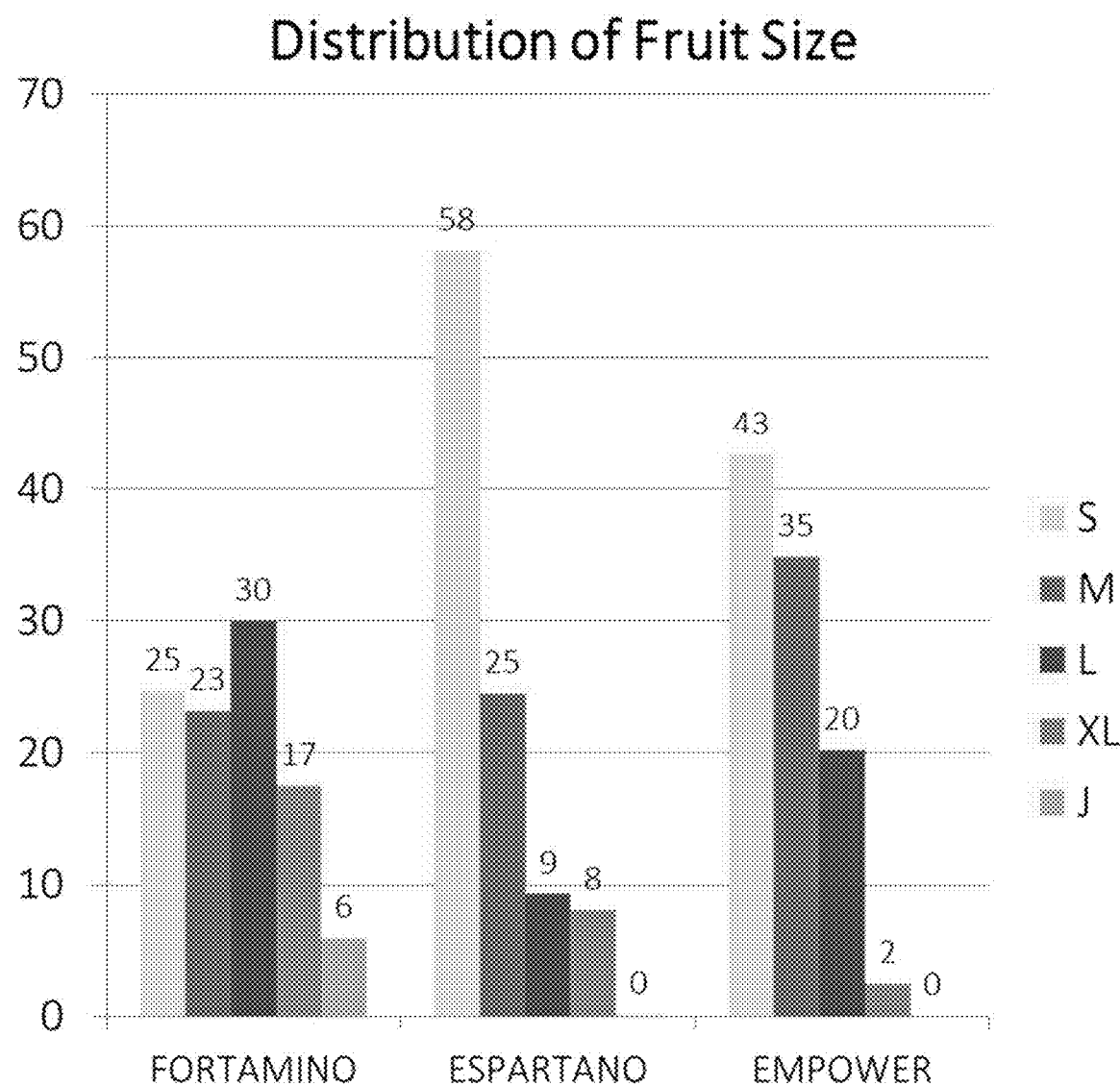
FIGS. 5A-5B show results of a first trial in which the scion 'Toretto' (unpatented) was grafted onto tomato rootstock 'Fortamino' (unpatented), hybrid tomato rootstock 'Espartano', and tomato rootstock 'Empower' (unpatented).
Figure 5B:
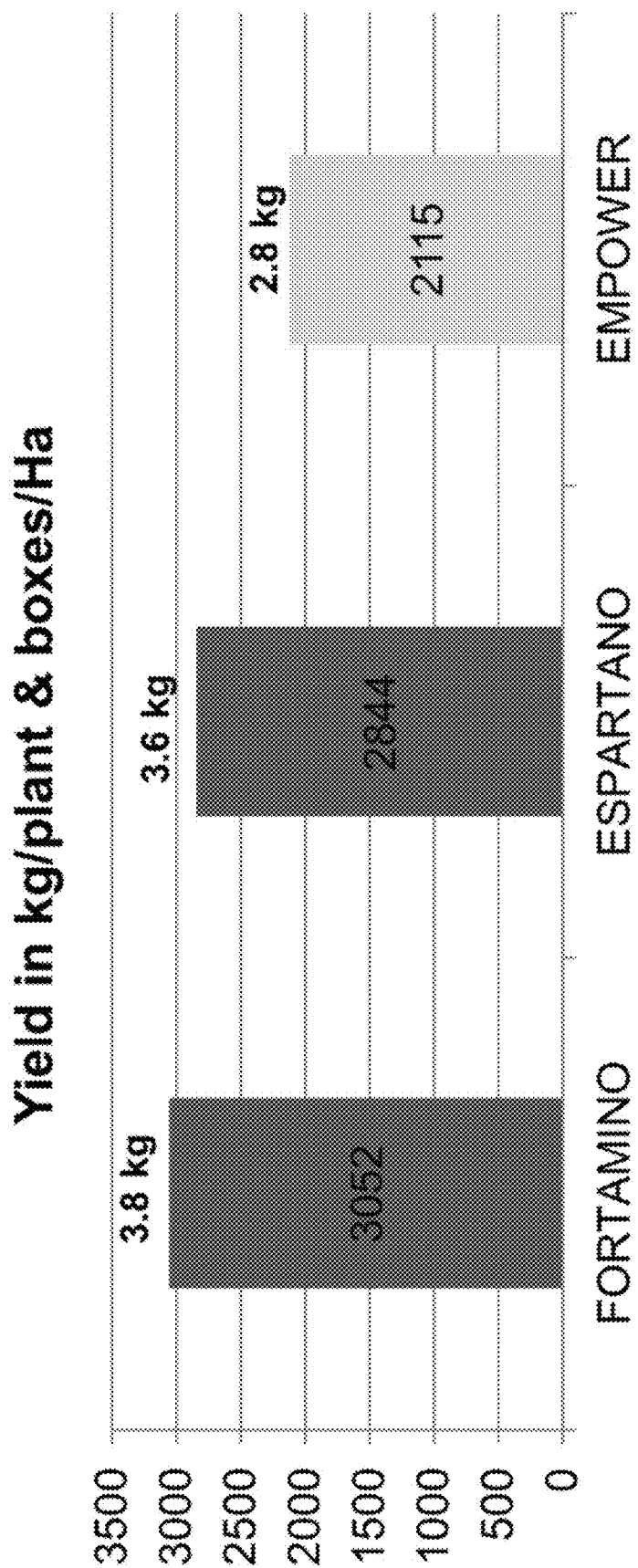

FIGS. 5A-5B show results of a first trial in which the scion 'Toretto' (unpatented) was grafted onto tomato rootstock 'Fortamino' (unpatented), hybrid tomato rootstock 'Espartano', and tomato rootstock 'Empower' (unpatented). FIG. 5A shows a comparison of fruit size produced by scion 'Toretto' when grafted onto tomato rootstock 'Fortamino', hybrid tomato rootstock 'Espartano', and tomato rootstock 'Empower'. FIG. 5B shows a comparison of yield of scion 'Toretto' when grafted onto tomato rootstock 'Fortamino', hybrid tomato rootstock 'Espartano', and tomato rootstock 'Empower'.

Figure 6:
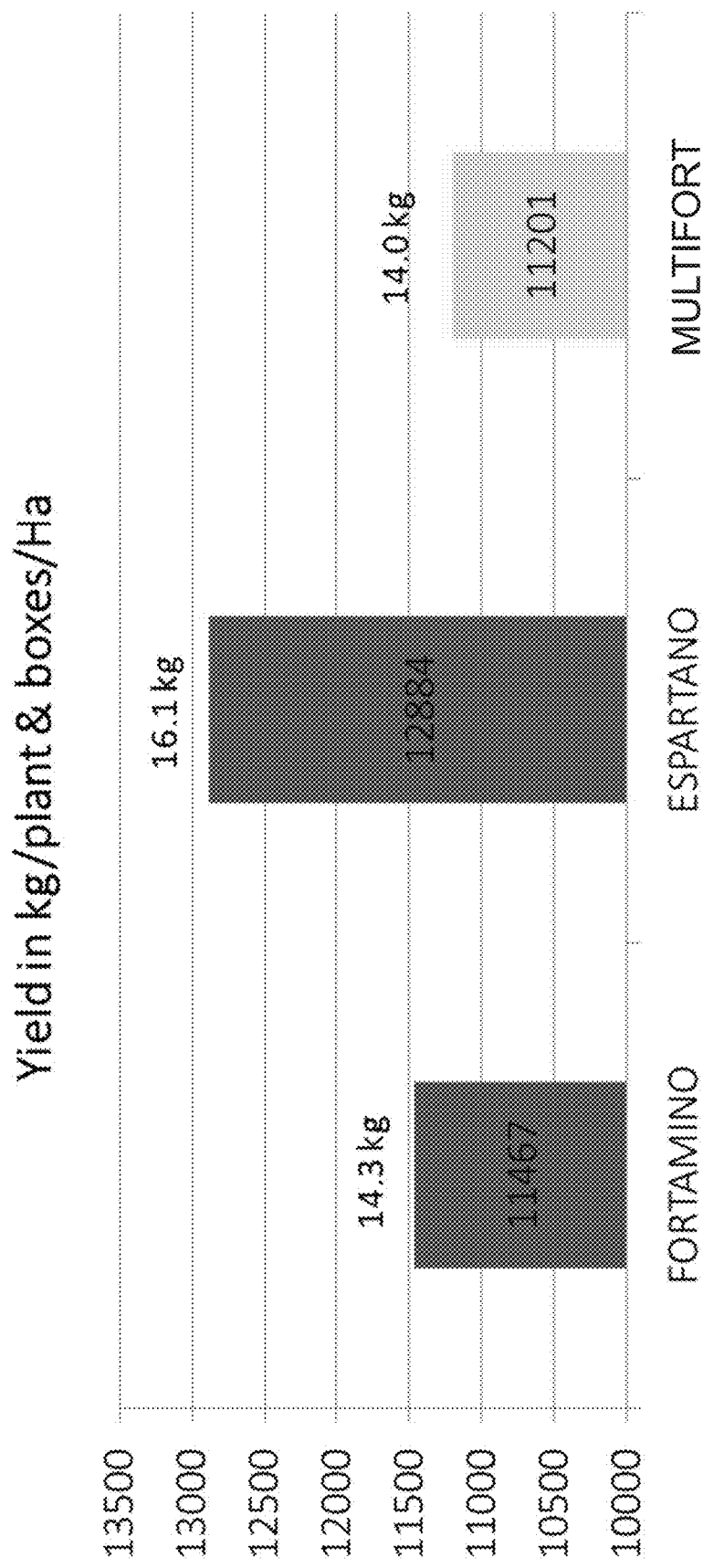
FIG. 6 shows results of a second trial in which the scion 'PaiPai' (unpatented) was grafted onto tomato rootstock 'Fortamino' (unpatented), hybrid tomato rootstock 'Espartano', and tomato rootstock 'Multifort' (unpatented), and the yield of scion 'PaiPai' when grafted onto tomato rootstock 'Fortamino', hybrid tomato rootstock 'Espartano', and tomato rootstock 'Multifort' was compared. The numbers above the bars are the yield in kg/plant, and the numbers inside the bars are the yield in boxes/Ha.

FIG. 6 shows results of a second trial in which the scion 'PaiPai' (unpatented) was grafted onto tomato rootstock 'Fortamino' (unpatented), hybrid tomato rootstock 'Espartano', and tomato rootstock 'Multifort' (unpatented). The yield of scion 'PaiPai' when grafted onto tomato rootstock 'Fortamino', hybrid tomato rootstock 'Espartano', and tomato rootstock 'Multifort' was compared.

Further Embodiments

The present disclosure is further directed to methods for producing a tomato plant by crossing a first parent tomato plant with a second parent tomato plant where either the first or second parent tomato plant is hybrid tomato 'E15T41376' or 'Espartano'. Further, both first and second parent tomato plants can come from hybrid tomato 'E15T41376' or 'Espartano'. All plants produced using hybrid tomato 'E15T41376' or 'Espartano' as a parent are within the scope of the disclosure, including plants derived from hybrid tomato 'E15T41376' or 'Espartano'.

Further, any methods using hybrid tomato 'E15T41376' or 'Espartano' are included in this disclosure: selfing, backcrosses, hybrid production, crosses to populations, and the like. Plants produced using hybrid tomato 'E15T41376' or 'Espartano' as a parent are presented herein, including plants derived from 'E15T41376' or 'Espartano'.

As used herein, the term plant includes plant cells, plant protoplasts, plant cell tissue cultures from which tomato plants can be regenerated, plant calli, plant clumps and plant cells that are intact in plants or parts of plants, such as embryos, pollen, ovules, flowers, leaves, stems, and the like.

Gene Conversions

When the terms "tomato plant", "hybrid", "cultivar", or "tomato line" are used in the context of the present disclosure, this also includes any single gene conversions of that variety. The term single gene converted plant as used herein refers to those tomato plants which are developed by a plant breeding technique called backcrossing wherein essentially all of the desired morphological and physiological characteristics of a variety are recovered in addition to the single gene transferred into the variety via the backcrossing technique. Backcrossing methods can be used with the present disclosure to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8 or more times to the recurrent parent. The parental tomato plant that contributes the gene for the desired characteristic is termed the nonrecurrent or donor parent. This terminology refers to the fact that the nonrecurrent parent is used one time in the backcross protocol and therefore does not recur. The parental tomato plant to which the gene or genes from the nonrecurrent parent are transferred is known as the recurrent parent as it is used for several rounds in the backcrossing protocol (Poehlman & Sleper, 1994; Fehr, Principles of Cultivar Development pp. 261-286 (1987)). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a tomato plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add an agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. Examples of single gene traits include, for example, male sterility, herbicide resistance, resistance for bacterial, fungal, or viral disease, insect resistance, male fertility, enhanced nutritional quality, industrial usage, yield stability, yield enhancement, modified fatty acid metabolism, modified carbohydrate metabolism, and nematode resistance. These genes are generally inherited through the nucleus. Several of these single gene traits are described in U.S. Pat. Nos. 5,959,185; 5,973,234, 5,777,196, 5,948,957, 5,969,212, and 5,977,445.

Tissue Culture

Further reproduction of a tomato variety can occur by tissue culture and regeneration. Tissue culture of various tissues of tomatoes and regeneration of plants therefrom is well known and widely published. For example, reference may be had to Girish-Chandel et al., Advances in Plant Sciences, 2000, 13: 1, 11-17; Costa et al., Plant Cell Report, 2000, 19: 3 327-332; Plastira et al., Acta Horticulturae, 1997, 447, 231-234; Zagorska et al., Plant Cell Report, 1998, 17: 12 968-973; Asahura et al., Breeding Science, 1995, 45: 455-459; Chen et al., Breeding Science, 1994, 44: 3, 257-262, Patil et al., Plant and Tissue and Organ Culture, 1994, 36: 2, 255-258; Gill, R., et al., Somatic Embryogenesis and Plant Regeneration from Seedling Cultures of Tomato (*Lycopersicon esculentum* Mill.), J. Plant Physiol., 147:273-276 (1995); Jose M. Segui-Simarro and Fernando Nuez, Embryogenesis induction, callogenesis, and plant regeneration by in vitro culture of tomato isolated microspores and whole anthers J. Exp. Bot., March 2007; 58: 1119-1132; Hamza et al., Re-evaluation of Conditions for Plant Regeneration and *Agrobacterium*-Mediated Transformation from Tomato (*Lycopersicon esculentum*), J. Exp. Bot., December 1993; 44: 1837-1845. It is clear from the literature that the state of the art is such that these methods of obtaining plants are routinely used and have a very high rate of success. Thus, another aspect of this disclosure is to provide cells which upon growth and differentiation produce tomato plants having the physiological and morphological characteristics of hybrid tomato 'E15T41376' or 'Espartano'.

As used herein, the term "tissue culture" indicates a composition containing isolated cells of the same or a different type or a collection of such cells organized into parts of a plant. Exemplary types of tissue cultures are protoplasts, calli, plant clumps, meristematic cells, and plant cells that can generate tissue culture that are intact in plants or parts of plants, such as embryos, pollen, flowers, seeds, fruit, petioles, leaves, stems, roots, root tips, anthers, pistils and the like. Means for preparing and maintaining plant tissue culture are well known in the art. By way of example, a tissue culture containing organs has been used to produce regenerated plants. U.S. Pat. Nos. 5,959,185; 5,973,234 and 5,977,445 describe certain techniques.

Vegetative Propagation

Tomato plants can also be propagated vegetatively. Accordingly, the present disclosure is further directed to vegetative propagation of hybrid tomato 'E15T41376' or 'Espartano'. A part of the plant, for example a shoot tissue, is collected and a new plant is obtained from the part. Such part typically includes an apical meristem of the plant. The collected part is transferred to a medium allowing development of a plantlet including, for example, rooting or development of shoots, or is grafted onto a tomato plant or a rootstock prepared to support growth of shoot tissue. This is achieved using methods well-known in the art. Accordingly, in one embodiment, a method of vegetatively propagating a tomato plant of the present disclosure involves collecting a part of a plant according to the present disclosure, e.g., a shoot tissue, and obtaining a plantlet from said part. In one embodiment, a method of vegetatively propagating a tomato plant of the present disclosure involves: a) collecting tissue of a plant of the present disclosure; and b) rooting said proliferated shoots to obtain rooted plantlets. In one embodiment, a method of vegetatively propagating a plant of the present disclosure involves: a) collecting tissue of a plant of the present disclosure; b) cultivating said tissue to obtain proliferated shoots; and c) rooting said proliferated shoots to obtain rooted plantlets. In one embodiment, such methods further involve growing a plant from said plantlets. In one embodiment, a fruit is harvested from said plant.

Additional Breeding Methods

Tomato varieties such as hybrid tomato 'E15T41376' or 'Espartano' are typically developed for use as fresh produce or for processing. However, tomato varieties also provide a source of breeding material that may be used to develop new tomato varieties. Plant breeding techniques known in the art and used in a tomato plant breeding program may include, for example, chasing selfs, recurrent selection, mass selection, bulk selection, mutation breeding, backcrossing, pedigree breeding, open pollination breeding, restriction fragment length polymorphism enhanced selection, genetic marker enhanced selection, making double haploids, and transformation. Often combinations of these techniques are used. The development of tomato varieties in a plant breeding program involves, in general, the development and evaluation of homozygous varieties. There are many analytical methods available to evaluate a new variety. The oldest and most traditional method of analysis is the observation of phenotypic traits, but genotypic analysis may also be used. Thus, another aspect of the disclosure is to provide hybrid tomato 'E15T41376' or 'Espartano' as a source of breeding material for the development of new tomato varieties using, for example, the breeding techniques described herein. One of skill in the art would recognize that additional breeding techniques may exist and may be used to develop new tomato varieties using hybrid tomato 'E15T41376' or 'Espartano'.

The present disclosure is directed to methods for producing a tomato plant by crossing a first parent tomato plant with a second parent tomato plant where either the first or second parent tomato plant is hybrid tomato 'E15T41376' or 'Espartano'. The other parent may be any other tomato plant, such as a tomato plant that is part of a synthetic or natural population. Further, both first and second parent tomato plants can come from tomato hybrid 'E15T41376' or 'Espartano'. Any such methods using hybrid tomato 'E15T41376' or 'Espartano' are part of this disclosure: selfing, sibbing, backcrosses, mass selection, pedigree breeding, bulk selection, hybrid production, crosses to populations, and the like. These methods are well known in the art and some of the more commonly used breeding methods are described herein. Descriptions of breeding methods can be found in one of several reference books (e.g., Allard, Principles of Plant Breeding, 1960; Simmonds, Principles of Crop Improvement, 1979; Sneep et al., 1979; Fehr, "Breeding Methods for Cultivar Development," 2.sup.nd ed., Wilcox editor, 1987).

All plants produced using tomato hybrid 'E15T41376' or 'Espartano' as at least one parent are within the scope of this invention, including those developed from cultivars derived from tomato hybrid 'E15T41376' or 'Espartano'.

Advantageously, the tomato cultivars of the present disclosure can be used in crosses with other, different, tomato plants to produce the first generation ($F_1$) tomato hybrid seeds and plants with superior characteristics. The cultivars of the invention can also be used for transformation where exogenous genes are introduced and expressed by the cultivars of the invention. Genetic variants created either through traditional breeding methods using tomato hybrid 'E15T41376' or 'Espartano' or through transformation of hybrid 'E15T41376' or 'Espartano' by any of a number of protocols known to those of skill in the art are within the scope of this invention.

The following describes exemplary breeding methods that may be used with hybrid tomato 'E15T41376' or 'Espartano' in the development of further tomato plants. One such embodiment is a method for developing a 'E15T41376' or 'Espartano' progeny tomato plant in a tomato plant breeding program involving: obtaining the tomato plant, or a part thereof, of 'E15T41376' or 'Espartano', utilizing said plant or plant part as a source of breeding material, and selecting a 'E15T41376' or 'Espartano' progeny plant with molecular markers in common with 'E15T41376' or 'Espartano' and/or with morphological and/or physiological characteristics selected from the characteristics listed in any one of Tables 1-4. Breeding steps that may be used in the tomato plant breeding programs may include pedigree breeding, back-crossing, mutation breeding, and recurrent selection. In conjunction with these steps, techniques such as RFLP-enhanced selection, genetic marker enhanced selection (for example SSR markers) and the making of double haploids may be utilized.

Another method involves producing a population of 'E15T41376' or 'Espartano' progeny tomato plants, involving crossing hybrid tomato 'E15T41376' or 'Espartano' with another tomato plant, thereby producing a population of tomato plants, which, on average, derive 50% of their alleles from 'E15T41376' or 'Espartano'. A plant of this population may be selected and repeatedly selfed or sibbed with a tomato cultivar resulting from these successive filial generations. In one embodiment, the tomato cultivar produced by this method has obtained at least 50% of its alleles from 'E15T41376' or 'Espartano'.

Additional methods include, without limitation, chasing selfs. Chasing selfs involves identifying inbred plants among tomato plants that have been grown from hybrid tomato seed. Once the seed is planted, the inbred plants may be identified and selected due to their decreased vigor relative to the hybrid plants that grow from the hybrid seed. By locating the inbred plants, isolating them from the rest of the plants, and self-pollinating them (i.e., "chasing selfs"), a breeder can obtain an inbred line that is identical to an inbred parent used to produce the hybrid.

Accordingly, another aspect of the present invention relates a method for producing an inbred tomato variety by: planting seed of the tomato variety 'E15T41376' or 'Espartano'; growing plants from the seed; identifying one or more inbred tomato plants; controlling pollination in a manner which preserves homozygosity of the one or more inbred plants; and harvesting resultant seed from the one or more inbred plants. The step of identifying the one or more inbred tomato plants may further include identifying plants with decreased vigor, i.e., plants that appear less robust than plants of the tomato variety 'E15T41376' or 'Espartano'. Tomato plants capable of expressing substantially all of the physiological and morphological characteristics of the parental inbred lines of tomato variety 'E15T41376' or 'Espartano' include tomato plants obtained by chasing selfs from seed of tomato variety 'E15T41376' or 'Espartano'.

One of ordinary skill in the art will recognize that once a breeder has obtained inbred tomato plants by chasing selfs from seed of tomato variety 'E15T41376' or 'Espartano', the breeder can then produce new inbred plants such as by sib-pollinating, or by crossing one of the identified inbred tomato plant with a plant of the tomato variety 'E15T41376' or 'Espartano'.

One of ordinary skill in the art of plant breeding would know how to evaluate the traits of two plant varieties to determine if there is no significant difference between the two traits expressed by those varieties. For example, see Fehr and Walt, Principles of Cultivar Development, p 261-286 (1987). Thus, the disclosure includes 'E15T41376' or 'Espartano' progeny tomato plants containing a combination of at least two traits of hybrid tomato 'E15T41376' or 'Espartano', the traits being selected from those listed in Tables 1-4, so that the progeny tomato plant is not significantly different for the traits than 'E15T41376' or 'Espartano' as determined at the 5% significance level when grown in the same environmental conditions. Using techniques described herein, molecular markers may be used to identify said progeny plant as an 'E15T41376' or 'Espartano' progeny plant. For each of the evaluation schemes involving hybrid tomato 'E15T41376' or 'Espartano', mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of 'E15T41376' or 'Espartano' may also be characterized through their filial relationship with 'E15T41376' or 'Espartano', as for example being within a certain number of breeding crosses of 'E15T41376' or 'Espartano'. A breeding cross is a cross made to introduce new genetics into the progeny, and is distinguished from a cross, such as a self or a sib cross, made to select among existing genetic alleles. The lower the number of breeding crosses in the pedigree, the closer the relationship between 'E15T41376' or 'Espartano' and its progeny. For example, progeny produced by the methods described herein may be within 1, 2, 3, 4 or 5 breeding crosses of 'E15T41376' or 'Espartano'.

Exemplary breeding techniques are further described herein and may be used in breeding schemes using hybrid tomato 'E15T41376' or 'Espartano'.

Backcross Conversion

Hybrid tomato 'E15T41376' or 'Espartano' represents new base genetic varieties into which a new locus or trait may be introgressed. Backcrossing represents an important method that can be used to accomplish such an introgression. The terms backcross conversion and single locus conversion are used interchangeably to designate the product of a backcrossing program.

A backcross conversion of a tomato variety such as, for example, hybrid tomato 'E15T41376' or 'Espartano', occurs when DNA sequences are introduced through backcrossing (Hallauer et al, 1988, "Corn Breeding" Corn and Corn Improvements, No. 18, pp. 463-481), with the tomato variety utilized as the recurrent parent. A backcross conversion may produce a plant with one or more desired genes or traits (e.g., 1, 2, 3, 4, or 5 and/or no more than 6, 5, 4, 3, or 2) in at least two or more backcrosses (e.g., at least 2, 3, 4, 5 or more crosses). Poehlman, Breeding Field Crops, P. 204 (1987) suggests from one to four or more backcrosses, but the number of backcrosses necessary can be reduced with the use of molecular markers. In addition, an herbicide resistance gene may be used as a selectable marker and/or as a phenotypic trait.

Other factors, such as a genetically similar donor parent, may also reduce the number of backcrosses necessary. As noted by Poehlman, 1987, backcrossing is easiest for simply inherited, dominant and easily recognized traits, but may be done with recessive alleles as well. The last backcross generation is usually selfed to give pure breeding progeny for the gene(s) being transferred, although a backcross conversion with a stably introgressed trait may also be maintained by further backcrossing to the recurrent parent with selection for the converted trait.

A single locus conversion of site specific integration system allows for the integration of multiple genes at the converted loci. Along with selection for the trait of interest, progeny are selected for the phenotype of the recurrent parent. The backcross is a form of inbreeding, and the features of the recurrent parent are automatically recovered after successive backcrosses (Poehlman, 1987).

While a number of exemplary methods are described above, any methods or combinations of methods for producing hybrid tomato 'E15T41376' or 'Espartano', and any methods or combinations of methods using hybrid tomato 'E15T41376' or 'Espartano' are included in the present disclosure. Descriptions of other breeding methods that are commonly used for different traits and crops can be found in one of several reference books (e.g., Allard, 1960; Simmonds, 1979; Sneep et al., 1979; Fehr, 1987). Additional non-limiting examples of methods that are known in the art of using and/or producing hybrid tomato 'E15T41376' or 'Espartano' include pedigree breeding, recurrent selection, mass selection, bulk selection, mutation breeding, open pollination breeding, restriction fragment length polymorphism enhanced selection, genetic marker enhanced selection, breeding with molecular markers, transformation, and production of double haploids.

Grafting Methods

Tomato rootstocks, such as hybrid tomato variety designated 'Espartano' may be grafted with a scion (i.e., a scion may be engrafted onto a rootstock) utilizing any suitable grafting methodology known in the art. Accordingly, any grafting methods using 'Espartano' are included the present disclosure. Examples of grafting methodologies include, without limitation, cleft grafting, approach grafting, micrografting, tube grafting, side insertion grafting, and top insertion grafting. Cleft grafting involves cutting a V-shape into the rootstock and inserting a complementing wedge-shaped scion. The graft may be then held with a small clip until healing occurs. Approach grafting, also known as tongue approach grafting (TAG), involves notching opposing sides of the stems of the rootstock and scion, and then using a clip to hold the stems together while they fuse. Once the graft has healed, the scion of the rootstock plant may be removed above the graft site, and the unused rootstock from the scion plant may be detached from the scion below the graft site. Micrografting, also known as splice grafting, is a technique that has been recently integrated into micropropagation production for hybrid tomato. Micrografting involves utilizing micropropagated scion shoots that may be grafted onto approximately three week-old rootstock seedlings. In some embodiments, micrografting is utilized for commercial scale tomato grafting. Tube grafting involves severing the scion and rootstock as seedlings and attaching the severed rootstock seedling to the severed scion seedling with a small, silicone tube with or without a clip. Tube grafting can be highly effective, as it may be carried out when plants are very small, thereby eliminating the need for large healing chambers while increasing the output. Although less frequently used on a commercial scale, side insertion grafting and top insertion grafting are also contemplated herein.

The use of the terms "a," "an," and "the," and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the embodiments of the disclosure and does not pose a limitation on the scope of the disclosure unless otherwise claimed. No language in the specification should be construed as indicating any non-claimed element as essential to the practice of the embodiments of the disclosure.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

DEPOSIT INFORMATION

Hybrid Tomato Rootstock 'Espartano'

A deposit of the hybrid tomato rootstock 'Espartano' is maintained by Enza Zaden USA, Inc., having an address at 7 Harris Place, Salinas, Calif. 93901, United States. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety with the National Collection of Industrial, Food and Marine Bacteria Ltd. (NCIMB Ltd), Ferguson Building, Craibstone Estate, Bucksburn, Aberdeen, AB21 9YA, United Kingdom.

At least 2500 seeds of hybrid tomato rootstock variety 'Espartano' were deposited on Aug. 31, 2020 according to the Budapest Treaty in the National Collection of Industrial, Food and Marine Bacteria Ltd (NCIMB Ltd), Ferguson Building, Craibstone Estate, Bucksburn, Aberdeen, AB21 9YA, United Kingdom. The deposit has been assigned NCIMB number 43655. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the NCIMB depository, which is a public depository, for a period of at least 30 years, or at least 5 years after the most recent request for a sample of the deposit, or for the effective life of the patent, whichever is longer, and will be replaced if a deposit becomes nonviable during that period.

The invention claimed is:

1. A hybrid tomato seed designated as 'Espartano', representative sample of seed having been deposited under NCIMB Accession Number 43655.

2. A tomato plant produced by growing the seed of claim 1.

3. A plant part from the plant of claim 2, wherein said part is a rootstock, a leaf, an ovule, a pollen grain, a fruit, or a cell.

4. The plant part of claim 3, wherein said part is a fruit or a rootstock.

5. A tomato plant having all the physiological and morphological characteristics of the tomato plant of claim 2.

6. A plant part from the plant of claim 5, wherein said part is a rootstock, a leaf, an ovule, a pollen grain, a fruit, or a cell.

7. The plant part of claim 6, wherein said part is a fruit or a rootstock.

8. A pollen grain or an ovule of the plant of claim 2.

9. A protoplast produced from the plant of claim 2.

10. A tissue culture of the plant of claim 2.

11. A tomato plant regenerated from the tissue culture of claim 10, wherein the plant has all of the morphological and physiological characteristics of a tomato plant produced by growing seed designated as 'Espartano', representative sample of seed having been deposited under NCIMB Accession Number 43655.

12. A method of making tomato seeds, said method comprising crossing the plant of claim 2 with another tomato plant and harvesting seeds therefrom.

13. A tomato plant comprising a rootstock and a scion engrafted onto the rootstock, wherein said rootstock is from hybrid tomato rootstock 'Espartano', representative sample of 'Espartano' tomato seed having been deposited under ATCC Accession Number 43655.

* * * * *